United States Patent [19]

Blaszczak et al.

[11] Patent Number: 4,492,693

[45] Date of Patent: Jan. 8, 1985

[54] BENZOTHIENYLGLYCYL CEPHALOSPORIN DERIVATIVES

[75] Inventors: Larry C. Blaszczak, Indianapolis; Stjepan Kukolja; Jan R. Turner, both of Carmel, all of Ind.

[73] Assignee: Eli Lilly and Company, Indianapolis, Ind.

[21] Appl. No.: 484,129

[22] Filed: Apr. 12, 1983

[51] Int. Cl.$^3$ .................. A61K 31/545; C07D 501/22
[52] U.S. Cl. ..................... 424/246; 544/21; 544/22; 544/28; 549/58
[58] Field of Search .................. 424/246; 544/22, 28, 544/21

[56] References Cited

U.S. PATENT DOCUMENTS

| | | | |
|---|---|---|---|
| 3,560,489 | 2/1971 | Morin | 544/25 |
| 3,575,969 | 4/1971 | Morin et al. | 544/28 |
| 4,024,133 | 5/1977 | Cook et al. | 544/28 |

Primary Examiner—Paul M. Coughlan, Jr.
Attorney, Agent, or Firm—Charles W. Ashbrook

[57] ABSTRACT 7-(3-Benzothienyl)glycylamido cephalosporins have good gram positive activity and favorable pharmacokinetics and are orally effective.

40 Claims, No Drawings

BENZOTHIENYLGLYCYL CEPHALOSPORIN DERIVATIVES

BACKGROUND OF THE INVENTION

The cephalosporin class of antibiotics has been extensively studied, and several members of the class are now routinely used to combat bacterial diseases caused by a broad spectrum of gram positive and gram negative microorganisms. The majority of such compounds are not effective orally, but rather are administered intramuscularly or intravenously, thus necessitating assistance from medically trained personnel. Moreover, since the compounds are effective against a broad spectrum of microorganisms, they generally are not employed for their specificity.

There remains a need for cepahlosporin antibiotics that are orally effective and have a degree of specificity toward one or more groups of microorganisms. An object of this invention is to provide a group of compounds that satisfy these needs.

SUMMARY OF THE INVENTION

This invention concerns cephalosporin antibiotics. The invention is more particularly directed to a group of (3-benzothienyl)glycylamido cephalosporin derivatives having the formula

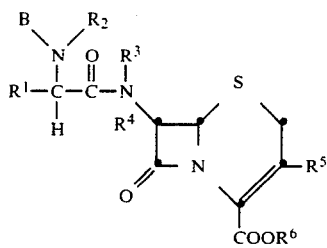

wherein:

$R^1$ is

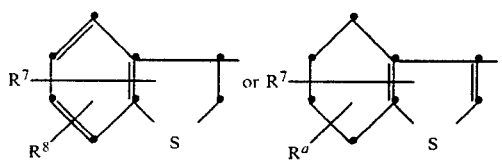

in which $R^7$ and $R^8$ independently are hydrogen, halo, hydroxy, $C_1$–$C_4$ alkyl, $C_1$–$C_4$ alkoxy, nitro, amino, $C_1$–$C_4$ alkanoylamino, $C_1$–$C_4$ alkylsulfonylamino, and when $R^7$ and $R^8$ are on adjacent carbon atoms, they can be taken together to form methylenedioxy;

A and B both are hydrogen, or taken together complete a double bond;

$R^2$ is hydrogen, an amino protecting group, hydroxy, or methoxy, and $R^3$ is hydrogen, or $R^2$ and $R^3$ taken together are

where

M and N independently are $C_1$–$C_4$ alkyl;

$R^4$ is hydrogen, methoxy or methylthio;

$R^5$ is hydrogen, methoxy, methyl, halo, methoxymethyl, or vinyl;

$R^6$ is hydrogen, a salt forming cation group, or a carboxy protecting group;

and the pharmaceutically acceptable acid addition salts thereof; with the proviso that $R^2$ is hydroxy or methoxy only when A and B complete a double bond, and that A and B both are hydrogen when $R^3$ is other than hydrogen.

Preferred compounds provided by the invention include those of the above formula wherein $R^1$ is

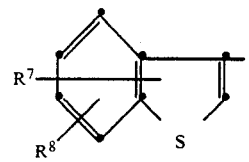

and $R^7$ and $R^8$ are as defined above. Within this group, preferred compounds include those wherein $R^2$ is hydrogen, an amino protecting group, hydroxy or methoxy, and $R^6$ is hydrogen or a carboxy protecting group.

Another preferred group of compounds are those wherein $R^1$ is

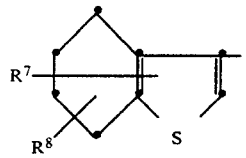

and $R^7$ and $R^8$ are as defined above. Especially preferred compounds within this group include those wherein A, B, $R^2$, $R^3$, $R^4$ and $R^6$ all are hydrogen.

A particularly preferred group of compounds provided by this invention are defined by the formula

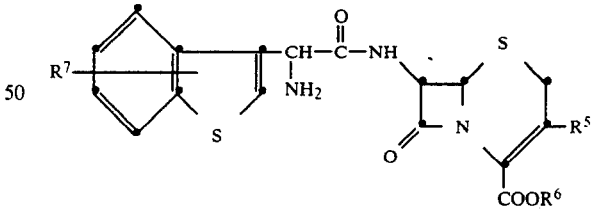

wherein $R^5$, $R^6$ and $R^7$ are as defined above. The most preferred compounds are those within this group wherein $R^7$ is hydrogen, halo, hydroxy or methoxy, $R^5$ is methyl or chloro, and $R^6$ is hydrogen or a salt forming group such as sodium or potassium cation.

An additional embodiment of this invention is a pharmaceutical formulation comprising a benzothienylglycylamino cephalosporin derivative as defined above admixed with a pharmaceutical carrier, diluent or excipient therefor. A preferred formulation is one suitable for oral administration.

Yet another embodiment of this invention is a method for treating bacterial infections in animals comprising administering an effective amount of an antibacterial compound of the above formula. In a preferred method of treatment, the benzothienylglycyl cephalosporin derivative is administered orally to treat diseases caused by gram positive microorganisms.

DETAILED DESCRIPTION OF THE INVENTION

In the above formulas defining the compounds provided by this invention, $R^1$ defines a 3-benzothienyl group of the formula

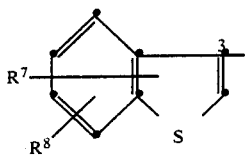

or a 3-(4,5,6,7-tetrahydrobenzothienyl) group of the formula

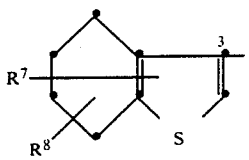

These benzothienyl and tetrahydrobenzothienyl groups can be unsubstituted, for instance when $R^7$ and $R^8$ both are hydrogen; or mono-substituted, for instance when one of $R^7$ or $R^8$ is hydrogen and one is other than hydrogen; or di-substituted, for instance when $R^7$ and $R^8$ both are other than hydrogen. $R^7$ can be located at the 2-position of the bicyclic ring system, or at the 4, 5, 6 or 7 position. $R^7$ and $R^8$ are defined above to include $C_1$–$C_4$ alkyl, $C_1$–$C_4$ alkoxy, halo, $C_1$–$C_4$ alkanoylamino and $C_1$–$C_4$ alkylsulfonylamino. The term "$C_1$–$C_4$ alkyl" carries its art-recognized meaning of straight and branched lower alkyl carbon chains such as methyl, ethyl, isopropyl, n-propyl, iso-butyl and tert.-butyl. Similarly, "$C_1$–$C_4$ alkoxy" refers to lower alkyl groups bonded to the benzothienyl or tetrahydrobenzothienyl bicyclic ring through an oxygen atom. Typical $C_1$–$C_4$ alkoxy groups include methoxy, ethoxy, n-propoxy, n-butoxy and iso-butoxy. The term "halo" as used herein includes fluoro, chloro, bromo and iodo. Preferred halo groups include chloro and fluoro.

$R^7$ and $R^8$ also represent $C_1$–$C_4$ alkanoylamino and $C_1$–$C_4$ alkylsulfonylamino. Typical alkanoylamino groups include formylamino, acetylamino, and isobutyrylamino. Typical $C_1$–$C_4$ alkylsulfonylamino groups are methylsulfonylamino, ethylsulfonylamino and n-butylsulfonylamino.

When $R^7$ and $R^8$ are on adjacent carbon atoms, they can be taken together to form a methylenedioxy group, for example to form an $R^1$ substituent such as

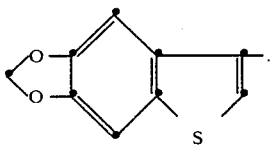

$R^2$ in the above formula defines a substituent on the glycyl nitrogen atom, and includes hydrogen and an amino protecting group. The term "amino protecting group" refers to any of the art-recognized substituents that can be attached to an amino nitrogen atom and which is readily removed when desired. Such protecting groups are often employed during preparation of the compounds of the invention, and serve to improve solubility in organic solvents and to decrease the likelihood of unwanted side reactions occurring as a result of the presence of a free amino group. While the compounds wherein $R^2$ is a protecting group are expected to have biological activity, it is contemplated that the most biologically desirable compounds will be those wherein $R^2$ is hydrogen. The compounds wherein $R^2$ is an amino protecting group are thus primarily useful as intermediates in the synthesis of the more preferred free amino compounds.

The precise nature of the amino protecting group is not critical to the invention, and any of the well known protecting groups can be employed. Typical amino protecting groups are described by J. W. Barton in "Protective Groups in Organic Chemistry," J. F. McOmie, Ed., Plenum Press, New York, N.Y., 1973, Chapter 2, and by Greene in "Protective Groups in Organic Synthesis," John Wiley and Sons, New York, N.Y., 1981, Chapter 7. Both of these references are incorporated herein by reference for their teaching of amino protecting groups.

The most common amino protecting groups to be employed include $C_1$–$C_{10}$ alkanoyl groups such as formyl, acetyl, dichloroacetyl, propionyl, hexanoyl 3,3-diethylhexanoyl, γ-chlorobutyryl, and the like; $C_1$–$C_{10}$ alkoxycarbonyl and $C_5$–$C_{15}$ aryloxycarbonyl groups such as tert.-butoxycarbonyl, benzyloxycarbonyl, allyloxycarbonyl, 4-nitrobenzyloxycarbonyl and cinnamoyloxycarbonyl; halo-$C_1$–$C_{10}$ alkoxycarbonyl such as 2,2,2-trichloroethoxycarbonyl; and $C_1$–$C_{15}$ arylalkyl and alkenyl groups such as benzyl, phenethyl, allyl, trityl, and the like. Other commonly used amino protecting groups are those in the form of enamines prepared with β-keto-esters such as methyl or ethyl acetoacetate.

$R^2$ in the above formula, in addition to representing hydrogen or an amino protecting group, also, when taken together with $R^3$, completes a ring system to provide compounds of the formula

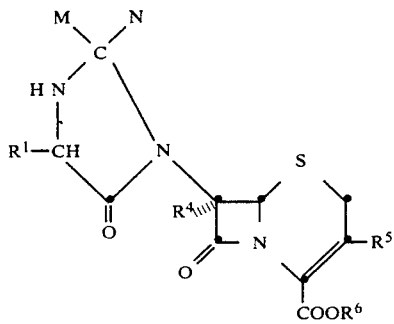

where $R^1$, $R^4$, $R^5$, $R^6$, M and N are as defined above. Typical of these compounds are the acetonides, for example those wherein M and N both are methyl and y is zero. Such compounds are particularly useful as long-acting antibacterial agents.

$R^6$ in the above formula is hydrogen; a salt forming group such as ammonium or an alkali metal cation, for example lithium, sodium or potassium; or a carboxy protecting group. The term "carboxy protecting group" refers to the art-recognized groups commonly employed to block or protect the carboxylic acid functionality of a cephalosporin molecule during chemical reactions involving other functional sites in the molecule, and which can be readily removed when desired by common hydrolytic or hydrogenolytic techniques. Typical carboxy protecting groups to be employed according to this invention include those described by E. Haslam in "Protective Groups in Organic Chemistry,", supra, Chapter 5, and by Greene in "Protective Groups in Organic Synthesis," supra, Chapter 5, which are incorporated herein by reference. Examples of the commonly employed carboxy protecting groups include $C_1$–$C_{10}$ alkyl groups such as methyl, tert.-butyl, decyl; halo-$C_1$–$C_{10}$ alkyl such as 2,2,2-trichloroethyl, and 2-iodoethyl; $C_5$–$C_{15}$ arylalkyl such as benzyl, 4-methoxybenzyl, 4-nitrobenzyl, triphenylmethyl, diphenylmethyl; $C_1$–$C_{10}$ alkanoyloxymethyl such as acetoxymethyl, propionoxymethyl and the like; and groups such as phenacyl, 4-halophenacyl, allyl, dimethylallyl, tri($C_1$–$C_3$ alkyl)silyl such as trimethylsilyl, β-p-toluenesulfonylethyl, β-p-nitrophenylthioethyl, 2,4,6-trimethylbenzyl, β-methylthioethyl, phthalimidomethyl, 2,4-dinitrophenylsulphenyl, 2-nitrobenzhydryl and related groups.

The benzothienylglycyl cephalosporin derivatives provided by this invention can be prepared by any of several methods. A preferred method comprises reacting a 7-aminocephalosporin nucleus with a benzothienylglycine derivative according to the following scheme:

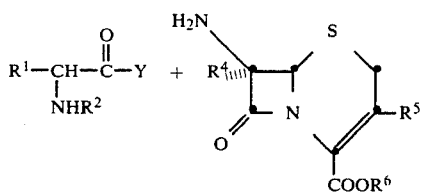

wherein $R^1$, $R^2$, $R^4$, $R^5$ and $R^6$ are as defined above, and Y is a leaving group such as hydroxy; halo, for instance chloro, bromo, or iodo; lower alkanoyloxy such as formyloxy, acetoxy or the like. Typical benzothienylglycine derivatives commonly employed in such direct coupling reactions include those of the formula

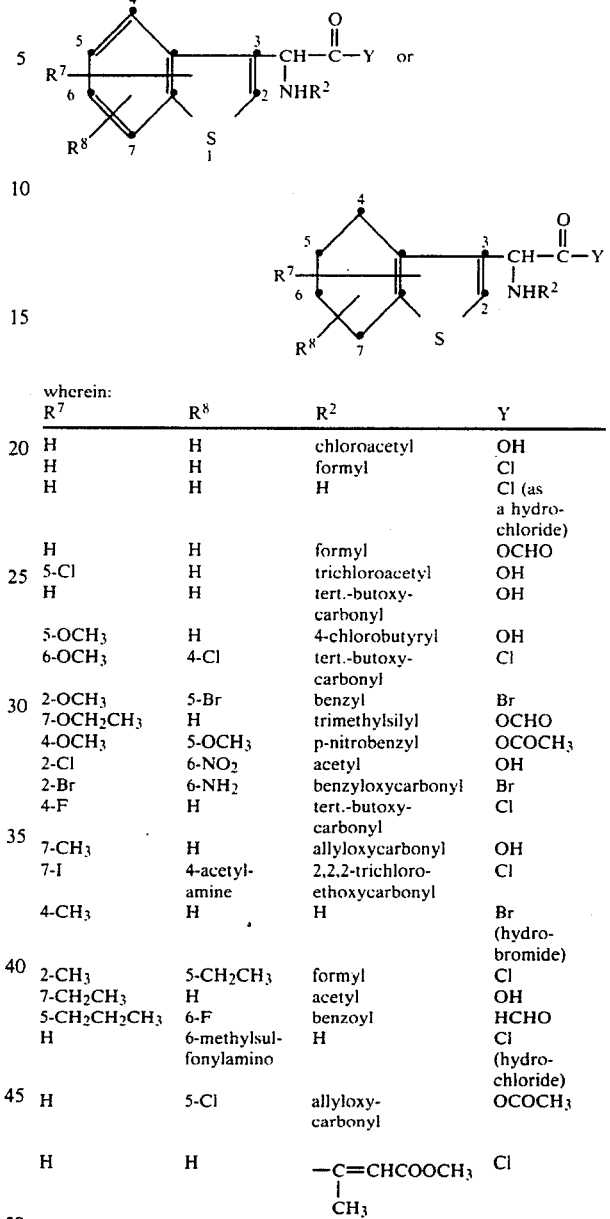

wherein:

| $R^7$ | $R^8$ | $R^2$ | Y |
|---|---|---|---|
| H | H | chloroacetyl | OH |
| H | H | formyl | Cl |
| H | H | H | Cl (as a hydrochloride) |
| H | H | formyl | OCHO |
| 5-Cl | H | trichloroacetyl | OH |
| H | H | tert.-butoxycarbonyl | OH |
| 5-OCH$_3$ | H | 4-chlorobutyryl | OH |
| 6-OCH$_3$ | 4-Cl | tert.-butoxycarbonyl | Cl |
| 2-OCH$_3$ | 5-Br | benzyl | Br |
| 7-OCH$_2$CH$_3$ | H | trimethylsilyl | OCHO |
| 4-OCH$_3$ | 5-OCH$_3$ | p-nitrobenzyl | OCOCH$_3$ |
| 2-Cl | 6-NO$_2$ | acetyl | OH |
| 2-Br | 6-NH$_2$ | benzyloxycarbonyl | Br |
| 4-F | H | tert.-butoxycarbonyl | Cl |
| 7-CH$_3$ | H | allyloxycarbonyl | OH |
| 7-I | 4-acetylamine | 2,2,2-trichloroethoxycarbonyl | Cl |
| 4-CH$_3$ | H | H | Br (hydrobromide) |
| 2-CH$_3$ | 5-CH$_2$CH$_3$ | formyl | Cl |
| 7-CH$_2$CH$_3$ | H | acetyl | OH |
| 5-CH$_2$CH$_2$CH$_3$ | 6-F | benzoyl | HCHO |
| H | 6-methylsulfonylamino | H | Cl (hydrochloride) |
| H | 5-Cl | allyloxycarbonyl | OCOCH$_3$ |
| H | H | —C=CHCOOCH$_3$<br>\|<br>CH$_3$ | Cl |

The benzothienylglycine derivatives thus described are either known commercially or are available by methods generally familar to those skilled in the art of organic chemistry. For example, British Pat. No. 1,399,089 describes the synthesis of 3-benzothienyl glyoxylic acids and oximes, the latter being readily convertible to benzothienylglycines. U.S. Pat. No. 3,976,680 describes a method for preparing optically pure benzothienylglycines. While any of these procedures can be employed to prepare benzothienylglycine derivatives, a preferred method of synthesis comprises reacting a benzothiophene or a tetrahydrobenzothiophene with an α-hydroxyglycine in the presence of trifluoroacetic acid. Such process provides directly, in high yield, a 3-benzothienylglycine or a 3-tetrahydrobenzothienylglycine that can be employed to prepare the compounds of this invention.

Like the benzothienylglycine starting materials, the cephalosporin nuclei required for the synthesis of the present compounds are readily available or can be prepared by methods well known in the art. For example, the 3-halo cephalosporin nuclei can be prepared by the methods taught in U.S. Pat. No. 3,925,372. 3-Methyl cephalosporins are available by ring expansion of penicillin sulfoxides and subsequent side chain cleavage. The 3-vinyl cephem nucleus is available by the method of U.S. Pat. No. 3,994,884.

Typical cephalosporin nuclei that will be employed in the synthesis of compounds of the present invention are illustrated below:

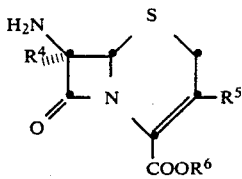

| $R^4$ | $R^5$ | $R^6$ |
|---|---|---|
| H | $CH_3$ | H |
| H | $CH_3$ | tert.-butyl |
| H | Cl | p-nitrobenzyl |
| $CH_3O$ | H | methyl |
| $CH_3S$ | $CH_3$ | H |
| H | $-CH_2OCH_3$ | 2,2,2-trichloroethyl |
| H | $-CH=CH_2$ | benzyl |
| H | $OCH_3$ | allyl |
| $CH_3O$ | Br | trimethylsilyl |
| $CH_3S$ | H | tert.-butyl |
| H | I | Na |

The coupling of a benzothienylglycine derivative with a 7-aminocephalosporin nucleus can be accomplished employing common techniques of acylation. For example, a benzothienylglycyl acylating agent, wherein Y in the above formula is a leaving group such as halo, especially chloro or bromo, or alkanoyloxy such as formyloxy or acetoxy, can be reacted with a cephalosporin nucleus employing standard acylation conditions. During such acylation reaction, it generally is preferred that $R^2$ in the above formula be an amino protecting group and that $R^6$ be a carboxy protecting group. These protecting groups serve to minimize unwanted side reactions and to increase solubility characteristics of the respective reactants.

The acylation reaction generally is accomplished by combining approximately equimolar quantities of a benzothienylglycyl acylating agent (i.e. an acid halide or mixed acid anhydride) with the 7-aminocephalosporin nucleus. The acylation reaction normally is carried out in a mutual solvent such as benzene, chloroform, dichloromethane, toluene, N,N-dimethylformamide, acetonitrile, or the like, and routinely is substantially complete after about 1 to about 12 hours when conducted at a temperature of about −20° to about 60° C. About an equimolar quantity of a base such as pyridine, triethylamine, aniline, sodium carbonate or the like, can be employed in the reaction if desired to act as an acid scavenger. The product may be isolated from the reaction mixture by simply removing the reaction solvent, for instance by evaporation under reduced pressure, and further purification can be accomplished if needed employing routine techniques such as chromatography, crystallization, solvent extraction, and related methods.

An alternative and preferred method for coupling a benzothienylglycine derivative to a 7-aminocephalosporin nucleus to produce compounds of the invention employs a coupling reagent such as those routinely used in the synthesis of peptides. Typical coupling reagents that can be employed include carbodiimides such as N,N′-diethylcarbodiimide, N,N-diisopropylcarbodiimide, and N,N-dicyclohexylcarbodiimide (DCC); carbonyl coupling reagents such as carbonyldiimidazole; isoxazolinium salts such as N-ethyl-5′-phenylisoxazolinium-3′-sulfonate; and quinoline compounds such as N-ethoxycarbonyl-2-ethoxy-1,2-dihydroquinoline (EEDQ).

The coupling of a 7-aminocephalosporin nucleus with a benzothienylglycine derivative employing a peptide coupling reagent generally is accomplished by combining approximately equimolar quantities of a 7-aminoceph-3-em-4-carboxylic acid, a benzothienylglycine, and a peptide coupling reagent according to the following scheme;

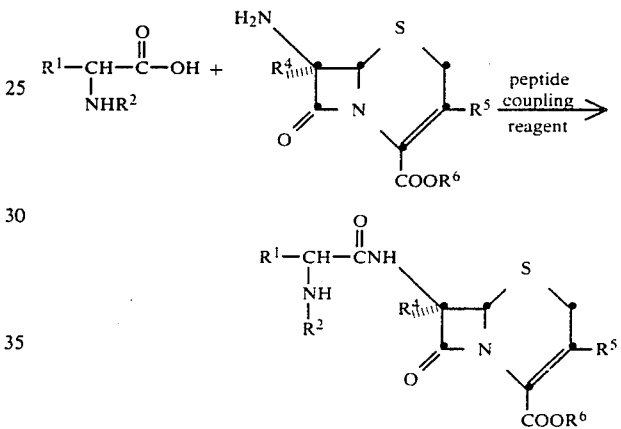

wherein $R^1$, $R^2$, $R^4$, $R^5$ and $R^6$ are as defined above. Preferably $R^2$ is an amino protecting group and $R^6$ is hydrogen or a carboxy protecting group during such coupling reactions. Any such protecting groups can be subsequently removed by standard methods to give the active antibiotic of the invention.

The coupling reaction normally is conducted in a mutual solvent such as dichloromethane, acetone, water, acetonitrile, N,N-dimethylformamide, chloroform, or the like, and routinely is substantially complete when carried out for about ten to about ninety minutes at a temperature of about −20° to about 60° C. Longer reaction periods are not detrimental to the product and can be employed if desired. The product, a benzothienylglycyl cephalosporin derivative of the invention, is readily isolated by simply removing the reaction solvent, for instance by evaporation under reduced pressure. The product can be purified if needed by standard methods such as acid-base extraction, chromatography, salt formation or the like.

Yet another alternative method for preparing compounds of the invention comprises chemically modifying a position other than the side chain of a benzothienylglycyl cephalosporin. For example, a 3-exomethylene cephalosporin nucleus can be acylated with a benzothienylglycyl derivative to form a benzothienylglycyl 3-exomethylene cephalosporin. The latter compound can be converted by known methods to compounds of the invention. For instance, ozonolysis of a benzothienylglycyl 3-exomethylene cephalosporin affords a 3-hydroxy compound. Halogenation of a 3-hydroxy compound affords the 3-halo benzothienylglycyl cephalosporins of the invention, while reaction with a base and a methylating agent affords the 3-methoxy compounds of the invention.

Still another method for preparing compounds of the invention employs a benzothienyl oxime derivative of the formula

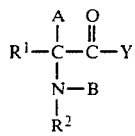

wherein $R^1$ and Y have the above-defined meanings, A and B are taken together to form a bond, and $R^2$ is hydroxy or methoxy. When $R^2$ is hydroxy, it generally is protected with trimethylsilyl, p-nitrobenzyl, or similar hydroxy protecting group during the coupling reaction. Such benzothienyl oxime derivatives can be coupled to a cephalosporin nucleus by any of the methods described above to provide a compound of the formula

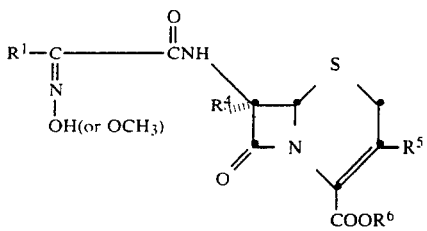

wherein $R^1$, $R^4$, $R^5$, and $R^6$ are as defined above. These compounds are useful as intermediates since they are readily reduced by normal methods to give the preferred benzothienylglycyl compounds of the invention. Additionally, the oximes of the above formula wherein $R^6$ is hydrogen or a salt forming group are useful antibiotics.

Compounds of the invention that bear a nitro group on the benzothienylglycyl or the tetrahydrobenzothienylglycyl side chain can be modified to provide other compounds of the invention. For example, the nitro substituent can be reduced by routine reduction or hydrogenation procedures to give the corresponding amino substituted benzothienylglycyl cephalosporin derivative, which if desired can be acylated by reaction with a $C_1$-$C_4$ alkanoyl halide or anhydride or a $C_1$-$C_4$ alkylsulfonyl halide to provide the corresponding alkanoylamino or alkylsulfonylamino benzothienylglycylamido cephalosporin of the invention.

Similarly, compounds of the invention wherein $R^2$ and $R^3$ are taken together to form the group

are prepared by reacting a ketone of the formula

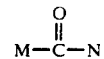

with a compound of the invention wherein $R^2$ and $R^3$ both are hydrogen, generally in the presence of a catalytic amount of an acid such as methanesulfonic acid or the like. The cyclic compounds thus produced, for instance the preferred acetonides wherein M and N both are methyl, are particularly useful as oral antibiotics since they are effective over prolonged periods of time.

Other compounds of the invention that are expected to be particularly long acting antibiotics are those wherein $R^2$ is an alkanoyl amino protecting group such as formyl or acetyl. Such compounds are conveniently prepared by simply reacting a benzothienylglycylamido cephalosporin, wherein $R^2$ is hydrogen, with a $C_1$-$C_{10}$ alkanoyl acylating agent, for instance formyl chloride or acetic anhydride. These N-acylated products are expected to act not only as antibiotics in themselves, but also as pro-drugs in that they will be hydrolyzed in an animal system to the parent benzothienylglycyl derivative.

It should be noted that since the benzothienylglycyl side chains of the cephalosporins of this invention contain one asymmetric carbon atom, for example when A is hydrogen, the compounds of the invention can exist in the form of optical isomers, namely the D and the L isomers of the side chain. The compounds of the invention can be employed as a DL-mixture to treat bacterial infections in animals, or if desired the isomers can be separated and employed individually. While both isomers are effective antibacterial agents, one isomer appears to be more potent than the other and is designated herein as the D-isomer, and accordingly is a preferred embodiment of the invention.

Separation or resolution of the isomers can be accomplished by routine methods carried out on the cephalosporin product of the invention or on the benzothienylglycine side chain that is employed as a starting material. Separation of isomers generally will be accomplished by high performance chromatography, enzymatic resolution, crystallization, or chemical resolution. A particularly preferred method for obtaining D-(3-benzothienyl)glycine comprises reacting the D,L-mixture with benzaldehyde and optically active tartaric acid according to the method of U.S. Pat. No. 3,976,680. Another preferred method of resolution employs an N-acyl L-amino acid amidohydrolase enzyme, for instance according to the method described in U.S. Pat. No. 3,386,888.

As noted above, preferred compounds of the invention are those wherein $R^2$ in the above formula is hydrogen. Such compounds, being primary amines, are basic in nature and readily form pharmaceutically acceptable salts by reaction with acids. Typical acids commonly employed to form salts include inorganic acids such as hydrogen chloride, hydrogen bromide, sulfuric acid, phosphoric acid; as well as organic acids such as acetic acid, trifluoroacetic acid, succinic acid, methanesulfonic acid, oxalic acid, para-toluenesulfonic acid, and the like. The compounds of the invention wherein both $R^2$ and $R^6$ are hydrogen readily form an internal acid addition salt, namely a zwitterion.

Examples of typical classes of benzothienylglycyl cephalosporins, as well as specific compounds provided by this invention, include those listed below:

Preferred Compounds of the formula

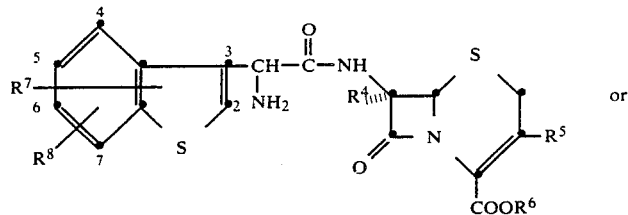

or

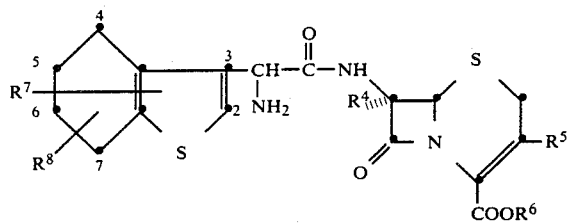

| R⁷ | R⁸ | R⁴ | R⁵ | R⁶ |
|---|---|---|---|---|
| H | H | H | CH₃ | H |
| H | H | H | Cl | H |
| H | H | H | CH=CH₂ | H |
| H | 4-Cl | H | H | Na⁺ |
| 2-OH | H | CH₃O— | CH₂OCH₃ | H |
| 4-Br | 7-CH₃ | H | OCH₃ | H |
| 2-CH₃ | 6-OCH₂CH₃ | CH₃S— | Br | NH₄⁺ |
| 5-F | 6-F | H | CH₃ | H |
| H | 6-NO₂ | H | CH₃ | K⁺ |
| H | 6-NH₂ | H | ·CH₃ | H |
| H | 6-NHCOCH₃ | CH₃O— | F | H |
| 2-Cl | 6-NHSO₂CH₂CH₃ | H | CH=CH₂ | H |
| 5-OCH₂CH(CH₃)₂ | H | H | H | tert-butyl |
| 6-OH | 7-CH₃ | CH₃S— | CH₂OCH₃ | p-nitrobenzyl |
| H | H | H | CH₃ | CH₂CH=CH₂ |
| H | H | H | Cl | CH₂CCl₃(hydrochloride) |
| 6-Cl | H | H | OCH₃ | trimethylsilyl |
| 5-CH₃ | H | H | CH₃ | H |
| 2-CH₃ | H | H | CH₃ | H |

Compounds of the formula

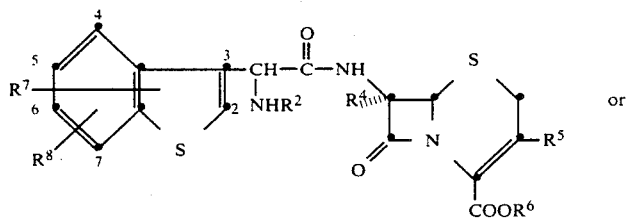

or

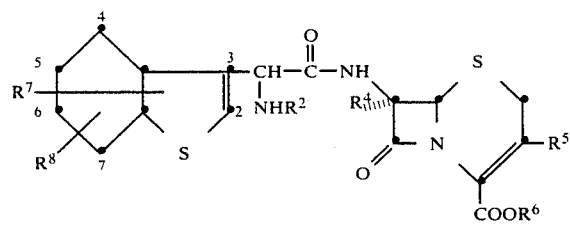

| R⁷ | R⁸ | R² | R⁴ | R⁵ | R⁶ |
|---|---|---|---|---|---|
| H | H | COOtert.butyl | H | CH₃ | H |
| H | H | COOCH₂CH=CH₂ | H | Cl | H |
| H | 6-OCH₃ | COCH₃ | CH₃O | H | H |
| 2-Cl | 6-OCH₃ | COOCH₂CCl₃ | H | OCH₃ | CH₂CCl₃ |
| 4-CH₃ | H | CH₂φ | H | CH₂OCH₃ | p-nitrobenzyl |
| 5-Br | 6-Br | C(φ)₃ | CH₃S | Br | CH₃ |
| H | 6-OH | CHO | H | CH=CH₂ | CH₂OCOCH₃ |

-continued

Compounds of the formula

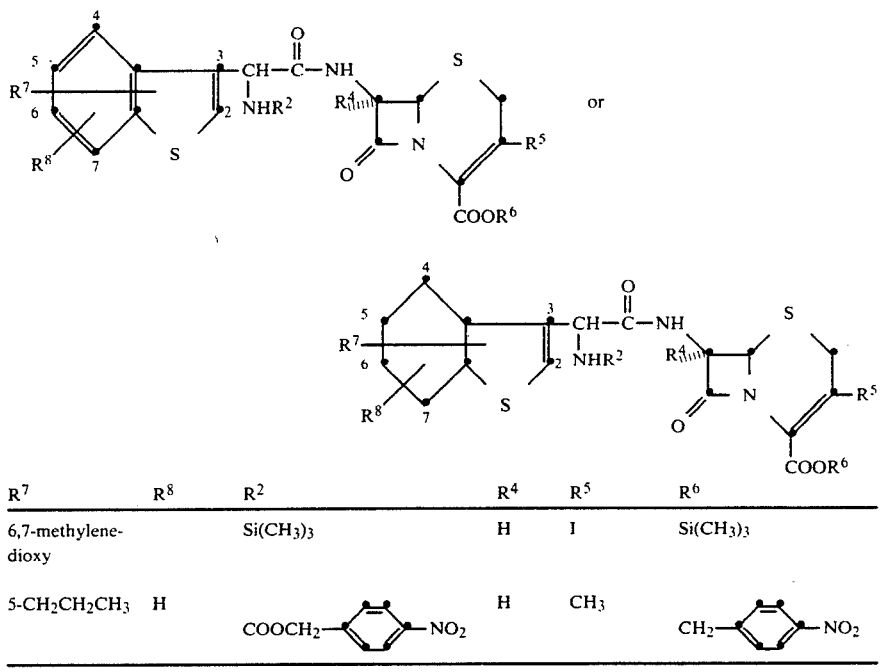

| R[7] | R[8] | R[2] | R[4] | R[5] | R[6] |
|---|---|---|---|---|---|
| 6,7-methylene-dioxy | Si(CH$_3$)$_3$ | | H | I | Si(CH$_3$)$_3$ |
| 5-CH$_2$CH$_2$CH$_3$ | H | COOCH$_2$-C$_6$H$_4$-NO$_2$ | H | CH$_3$ | CH$_2$-C$_6$H$_4$-NO$_2$ |

Compounds of the formula

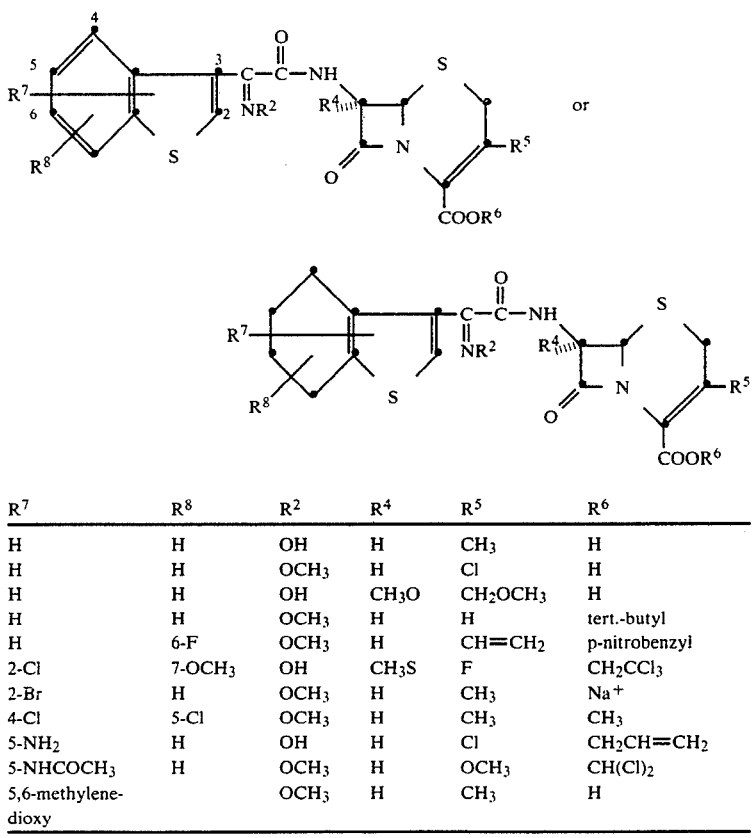

| R[7] | R[8] | R[2] | R[4] | R[5] | R[6] |
|---|---|---|---|---|---|
| H | H | OH | H | CH$_3$ | H |
| H | H | OCH$_3$ | H | Cl | H |
| H | H | OH | CH$_3$O | CH$_2$OCH$_3$ | H |
| H | H | OCH$_3$ | H | H | tert.-butyl |
| H | 6-F | OCH$_3$ | H | CH=CH$_2$ | p-nitrobenzyl |
| 2-Cl | 7-OCH$_3$ | OH | CH$_3$S | F | CH$_2$CCl$_3$ |
| 2-Br | H | OCH$_3$ | H | CH$_3$ | Na$^+$ |
| 4-Cl | 5-Cl | OCH$_3$ | H | CH$_3$ | CH$_3$ |
| 5-NH$_2$ | H | OH | H | Cl | CH$_2$CH=CH$_2$ |
| 5-NHCOCH$_3$ | H | OCH$_3$ | H | OCH$_3$ | CH(Cl)$_2$ |
| 5,6-methylene-dioxy | | OCH$_3$ | H | CH$_3$ | H |

Compounds of the formula

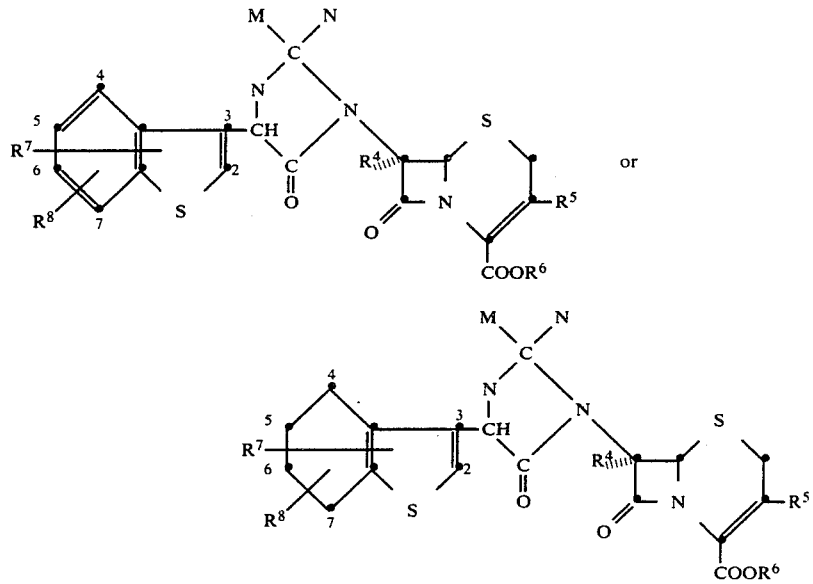

| R[7] | R[8] | M | N | R[4] | R[5] | R[6] |
|---|---|---|---|---|---|---|
| H | H | CH$_3$ | CH$_3$ | H | CH$_3$ | H |
| H | 5-F | CH$_3$ | CH$_3$ | H | Cl | Na$^+$ |
| H | 6-OCH$_3$ | CH$_3$ | CH$_3$ | H | CH$_3$O | OCH$_3$ | tert.-butyl |
| 2-Cl | H | CH$_3$ | CH$_3$ | CH$_3$S | H | H |
| 2-OCH$_3$ | 5-CH$_3$ | CH$_2$CH$_3$ | CH$_3$ | H | CH$_3$ | CH(O)$_2$ |
| 5-F | 6-F | CH$_3$ | CH$_3$ | H | CH=CH$_2$ | CH$_2$CH=CH$_2$ |

The synthesis of the compounds provided by this invention is further illustrated by the following preparations and working examples. The examples are illustrative only and are not intended to limit the invention in any respect.

PREPARATION 1

3-Benzothienylglycine

A. Preparation of Oxime

A solution of 97 g of 1-benzothiophene (thianaphthene) in 70 ml of acetic anhydride was heated to 60° C. and stirred while 17.5 ml of boron trifluoride diethyl etherate were added in one portion. The reaction mixture was stirred for ninety minutes and then was added to 300 ml of water. The aqueous mixture was extracted several times with diethyl ether, and the ethereal extracts were combined and concentrated to dryness to provide, following distillation, 69 g of 3-acetylbenzothiophene.

Eleven grams of the 3-acetylbenzothiophene from above was dissolved in 80 ml of pyridine and warmed to 60° C. To the reaction mixture were added portionwise 9.92 g of selenium dioxide. The reaction mixture was warmed to 120° C. and then cooled to 90° C. and stirred at that temperature for forty-five minutes. The mixture was next added to 80 ml of water, and the pyridine solvent was then removed by evaporation. The aqueous mixture was acidified to pH 2.0 with phosphoric acid, and the product was extracted into diethyl ether. Removal of the solvent by evaporation and crystallization of the product from benzene gave 3.85 g of 3-benzothienylglycolic acid. m.p. 89°–91° C.

Reaction of the above compound with hydroxylamine in methanol afforded 3.93 g of α-hydroxyimino-α-(3-benzothienyl)acetic acid.

The following compounds were also prepared for use as intermediates in the synthesis of compounds of the invention.

α-methoxyimino-α-(6-fluoro-3-benzothienyl)acetic acid m.p. 150°–151° C.;

α-methoxyimino-α-(4-fluoro-3-benzothienyl)acetic acid;

α-methoxyimino-α-(5-fluoro-3-benzothienyl)acetic acid;

α-methoxyimino-α-(7-fluoro-3-benzothienyl)acetic acid;

ethyl α-hydroxyimino-α-(4-methoxy-3-benzothienyl)acetate 49% yield (1.1 g);

ethyl α-oxo-α-(6-nitro-3-benzothienyl)acetate, m.p. 158°–160° C.;

ethyl α-oxo-α-(5-nitro-3-benzothienyl)acetate, m.p. 198°–200° C.;

ethyl α-oxo-α-(4-nitro-3-benzothienyl)acetate, m.p. 120° C.;

ethyl α-oxo-α-(7-nitro-3-benzothienyl)acetate, m.p. 140° C.;

α-methoxyimino-α-(6-methoxy-3-benzothienyl)acetic acid 90% yield;

ethyl α-hydroxyimino-α-(5-chloro-3-benzothienyl)acetate;

ethyl α-methoxyimino-α-(4-chloro-3-benzothienyl)acetate; and ethyl α-methoxyimino-α-(6-chloro-3-benzothienyl)acetate.

B. Reduction of oxime

To a stirred suspension of 4.0 g of 5% palladium on carbon in 200 ml of methanol were added in one portion 3.93 g of α-hydroxyimino-α-(3-benzothienyl)acetic acid. The reaction mixture was stirred at 24° C. for three hours under hydrogen at 60 psi. The reaction mixture was then diluted by addition of 21 ml of 1N hydrochloric acid, and stirring was continued for five minutes. The pH of the reaction mixture was adjusted to 4.3 with conc. sodium hydroxide and the precipitate that formed was collected and air dried to give 1.35 g of 3-benzothienylglycine. m.p. 195°–198° C.

The various substituted oximes mentioned above were reduced by catalytic hydrogenation or by reaction with zinc and an acid such as formic acid to provide the corresponding substituted 3-benzothienylglycines.

PREPARATION 2

Ethyl α-oxo-α-(α-amino-3-benzothienyl)acetate

To a stirred suspension of 1.1 g of 5% palladium on carbon in 100 ml of ethanol under 60 psi of hydrogen was added in one portion a solution of 1.1 g of ethyl α-oxo-α-(6-nitro-3-benzothienyl)acetate in 25 ml of tetrahydrofuran. The reaction mixture was stirred at 25° C. under 60 psi of hydrogen for forty-five minutes, and then the mixture was filtered and the solvent was evaporated from the filtrate to give ethyl α-oxo-α-(6-amino-3-benzothienyl)acetate. Reaction with methoxylamine and subsequent hydrolysis and hydrogenation provides (6-amino-3-benzothienyl)glycine.

Preparation of Amino protected benzothienylglycines

PREPARATION 3

N-(3-Chloropropylcarbonyl)-3-benzothienylglycine

A solution of 621 mg (3 mM) of 3-benzothienylglycine in 15 ml of dichloromethane containing 0.92 ml (6.6 mM) of triethylamine and 717 mg of chlorotrimethylsilane was heated at 50° C. and stirred for thirty minutes and then cooled to 5° C. A solution of 0.336 ml (3 mM) of 4-chlorobutyryl chloride in 5 ml of dichloromethane was added dropwise to the reaction mixture and stirring was continued at 5° C. for one hour following the addition. The reaction mixture was warmed to 25° C. and stirred for an additional hour. The reaction mixture was next washed twice with 10 ml portions of water, dried, and the solvent was removed by evaporation to give an oil. The oil was crystallized from 0.7 ml of acetone and 2.7 ml of water, and recrystallized from ethyl acetate to afford 150 mg of N-(3-chloropropylcarbonyl)-3-benzothienylglycine. m.p. 167°–168° C.

PREPARATION 4

Methyl acetoacetate enamine of benzothienylglycine

To a stirred suspension of 20.7 g (100 mM) of D,L-3-benzothienylglycine in 375 ml of isopropanol were added in one portion 3.93 g (100 mM) of sodium hydroxide. The reaction mixture was heated at reflux for one hour, cooled to about 50° C., and diluted by addition in one portion of 2.8 ml (26 mM) of methyl acetoacetate. The reaction mixture was heated at reflux for an additional ninety minutes and then cooled to 25° C. and stirred for sixteen hours. The precipitated solid was collected by filtration and air dried to provide 30.06 g (92% yield) of the methyl acetoacetate enamine of sodium D,L-3-benzothienylglycine. NMR (DMSOd$_6$): δ 1.70 (s, 3H); δ 3.48 (s, 3H); δ 4.2 (s, 1H); δ 7.1–7.4 (m, 3H); δ 7.7–8.2 (m, 2H); δ 9.62 (d, 1H).

The following amino protected benzothienylglycines were also prepared:

N-tert.-butoxycarbonyl-(3-benzothienyl)glycine 92% yield;

N-allyloxycarbonyl-(3-benzothienyl)glycine 86% yield;

N-chloroacetyl-(3-benzothienyl)glycine 83% yield;

N-(p-nitrobenzyloxycarbonyl)-(3-benzothienyl)glycine 76% yield;

N-tert.-butoxycarbonyl-(5-chloro-3-benzothienyl)glycine 66% yield;

N-tert.-butoxycarbonyl-(5-methoxy-3-benzothienyl)glycine.

The following preparations illustrate a preferred method for making benzothienylglycines.

PREPARATION 5

N-Allyloxycarbonyl-(3-benzothienyl)glycine

A solution of 5.15 g (29.4 mM) of DL N-allyloxycarbonyl-α-hydroxyglycine and 3.95 g (29.4 mM) of benzo[b]thiophene in 40 ml of trifluoroacetic acid was stirred at 22.5° C. for eighteen hours. The reaction mixture was then concentrated by evaporation under reduced pressure to given an oil, and the oil was dissolved in a mixture of 100 ml of ethyl acetate and 100 ml of water. The organic layer was separated, and the aqueous layer was extracted twice more with 50 ml portions of fresh ethyl acetate. The organic extracts were combined, washed with water, and then extracted twice with 100 ml portions of 10% aqueous sodium bicarbonate. The aqueous extracts were combined, added to 100 ml of fresh ethyl acetate, and acidified to pH 2.0 by the addition of conc. hydrochloric acid. The organic layer was separated and the aqueous acid layer was extracted with two 50 ml portions of fresh ethyl acetate. The organic portions were combined, dried, and the solvent was removed by evaporation to provide 7.55 g (88% yield) of N-allyloxycarbonyl-(3-benzothienyl)glycine.

Analysis calc. for $C_{14}H_{13}NO_4S$: Theory: C, 57.92; H, 4.50; N, 4.81; O, 21.97; S, 11.27. Found: C, 57.98; H, 4.57; N, 4.54; O, 21.80; S, 11.27.

Mass Spec. M+ Theory 291; Found 291.

pK$_a$ (66% aqueous DMF) 5.70

IR (KBr mull) 3313, 1711, 1683, 1543, 1420, 1312 cm$^{-1}$.

The following benzothienylglycines are similarly prepared:

N-allyloxycarbonyl-(5-methoxy-3-benzothienyl)glycine;

N-ethoxycarbonyl-(5-methoxy-3-benzothienyl)glycine yield 4.62 g (21%);

N-ethoxycarbonyl-(5-benzoyloxy-3-benzothienyl)glycine (subsequently hydrolyzed to N-ethoxycarbonyl(5-hydroxy-3-benzothienyl)glycine;

N-chloroacetyl-(5-methoxy-3-benzothienyl)glycine.

PREPARATION 6

D-(3-Benzothienyl)glycine

A solution of 4.3 g (19.4 mM) of the methyl ester of D,L-(3-benzothienyl)glycine in 65 ml of acetonitrile containing 2.6 ml (25.7 mM) of benzaldehyde and 2.88 g (19.4 mM) of (−)tartaric acid was heated for ten minutes in a boiling water bath. The reaction mixture was cooled to 24° C. and stirred for twenty-six hours. The reaction mixture was filtered, and the filter cake was dried in vacuum at 40° C. to give 6.095 g (85% yield) of the (−)tartaric acid salt of D-(3-benzothienyl)glycine methyl ester. m.p. 174°–176° C.

The product thus formed was suspended in 250 ml of dichloromethane and the mixture was added to 250 ml of 5% aqueous (wt/v) sodium bicarbonate. The mixture was stirred for ten minutes, and the organic layer was then separated, washed with fresh water, dried and the solvent was removed by evaporation to give 3.42 g (98% yield) of D-(3-benzothienyl)glycine methyl ester. $[\alpha]_D^{25} = -173.8°$ The ester thus formed (3.299 g, 14.93 mM) was dissolved in 13.7 ml of 2.22N sodium hydroxide. The reaction mixture was stirred for fifteen minutes, maintaining the temperature at about 25° C. by periodic immersion in cold water. The reaction mixture was acidified to pH 4.6 by addition of 2N hydrochloric acid, and diluted by addition of about 100 ml of water. The aqueous acid mixture was cooled to about 5° C. over about ninety minutes, and the precipitate was then removed by filtration and dried at 60° C. in vacuum to give 3.09 g (96% yield) of D-(3-benzothienyl)glycine. m.p. 203°–207° C. $[\alpha]_D^{25} = -182.6°$.

PREPARATION 7

Enzymatic resolution of D,L 3-benzothienylglycine

By following the general procedure of U.S. Pat. No. 3,386,888, 10.0 g of D,L-N-chloroacetyl-3-benzothienylglycine was reacted with an N-acyl L-amino acid amidohydrolase (immobilized on a 1¼ in.×33½ in chromatographic column). The chromatography was carried out at 37° C., eluting with 2000 ml of a 0.1M potassium hydrogen phosphate pH 7.0 buffer containing 10 ml of 0.1 M cobalt chloride hexahydrate and adjusted to pH 7.08 by addition of 5N sodium hydroxide. The flow rate was adjusted to 1.13 ml per minute, and the chromatography was complete in twenty-eight hours, fifteen minutes. Fractions shown by thin layer chromatography and amino acid assays to contain one product were combined and the pH was adjusted to 2.0 by addition of conc. hydrochloric acid. The acidic solution was extracted several times with ethyl acetate, and the extracts were combined, washed with water, dried and concentrated to dryness to give 4.4 g of D-N-chloroacetyl-3-benzothienylglycine. $[\alpha]_{589}^{25} -122.0°$; $[\alpha]_{365}^{25} -490.8°$.

PREPARATION 8

α-Methoxyimino-α-(6-methoxy-3-benzothienyl)acetic acid

To a stirred solution of sodium 3-methoxythiophenoxide in 150 ml of ethanol (prepared by reacting 14 g of 3-methoxythiophenol with 5.94 g of sodium methoxide) were added dropwise over ten minutes 27.7 g of ethyl 2-methoxyimino-3-oxo-4-bromobutyrate. The reaction mixture was stirred at 25° C. for sixteen hours, and then the solvent was removed by evaporation under reduced pressure to give an oil. The oil was dissolved in ethyl acetate and washed several times with water. The organic layer was dried and the solvent was removed by evaporation to afford 16.28 g of ethyl 2-methoxyimino-3-oxo-4-(3-methoxyphenylthio)butyrate. NMR (CDCl$_3$): δ1.32 (t, 3H); δ3.79 (s, 3H); δ4.05 (s, 3H); δ4.34 (q, 2H); δ6.7–7.3 (m, 4H).

Five grams of the compound from above was added to 40 ml of methane sulfonic acid, and the solution was stirred for fifteen minutes at 25° C. The reaction mixture then was added to 400 ml of ice water, and the aqueous mixture was extracted several times with diethyl ether. The ethereal extracts were combined, washed with water and with aqueous sodium bicarbonate, dried, and the solvent was removed by evaporation to give 4.31 g of ethyl α-methoxyimino-α-(6-methoxy-3-benzothienyl)acetate. NMR (CDCl$_3$): δ1.36 (t, 3H); 3.80 (s, 3H); δ4.02 (s, 3H); δ4.3 (q, 2H); δ6.8–7.2 (m, 3H); δ8.3 (d, 1H).

A solution of 2.65 g of the compound thus prepared in 50 ml of ethanol containing 3.6 ml of 5N sodium hydroxide was stirred at 25° C. for three and one-half hours. The solvent was then removed by evaporation to provide an oil, which was dissolved in ethyl acetate and water. The aqueous layer was separated and the organic layer was extracted with aqueous sodium bicarbonate. The aqueous portions were combined, acidified to pH 1.8 with 1N hydrochloric acid and extracted with fresh ethyl acetate. The organic extracted was dried and concentrated to give 1.39 g of α-methoxyimino-α-(6-methoxy-3-benzothienyl)acetic acid. NMR (DMSOd$_6$): δ3.82 (s, 3H); δ4.02 (s, 3H; δ7.04–8.41 (m, 4H).

PREPARATION 9

α-Methoxyimino-α-(6-fluoro-3-benzothienyl)acetic acid

A solution of 25.60 g of ethyl α-(6-fluoro-3-benzothienyl)acetate in 100 ml of ethanol containing 107 ml of 1M ethanolic sodium ethoxide and 17.5 ml of n-butyl nitrite was stirred at 24° C. for about twenty hours. The reaction mixture was diluted by addition of 300 ml of ethanol and 9.2 ml of glacial acetic acid and stirred for an additional one hour. The reaction mixture was then concentrated in volume, diluted with water, and the product was extracted into ethyl acetate. The ethyl acetate solution was washed with aqueous sodium bicarbonate, dried and the solvent was removed to provide, following crystallization from n-hexane and diethyl ether, 7.99 g of ethyl α-hydroxyimino-α-(6-fluoro-3-benzothienyl)acetate. m.p. 168°–171° C. Second crop of 10.25 g was also recovered. Yield 64.%.

Reaction of 7.82 g of the compound thus prepared with 4.16 ml of dimethyl sulfate and 5.53 g of potassium carbonate provided 3.59 g (48%) of ethyl α-methoxyimino-α-(6-fluoro-3-benzothienyl)acetate. m.p. 84.5°–86° C.

A solution of 3.50 g of ethyl α-methoxyimino-α-(6-fluoro-3-benzothienyl)acetate in 75 ml of ethanol containing 40 ml of 0.5N sodium hydroxide was stirred at 24° C. for nineteen hours. The solution was then concentrated to a volume of about 50 ml, and 50 ml of water were added. The aqueous solution was washed with dichloromethane, filtered, and then acidified to pH 2 by addition of 6N hydrochloric acid. The precipitate that formed was collected by filtration and identified as 3.02 g (95%) of α-methoxyimino-α-(6-fluoro-3-benzothienyl)acetic acid. m.p. 150°–151° C.

Similarly prepared were:

α-methoxyimino-α-(4-fluoro-3-benzothienyl)acetic acid;

α-methoxyimino-α-(5-fluoro-3-benzothienyl)acetic acid; and

α-methoxyimino-α-(7-fluoro-3-benzothienyl)acetic acid.

EXAMPLE 1 p-Nitrobenzyl 7-[N-(3-chloropropylcarbonyl)-3-benzothienyl]-glycylamido-3-methyl-3-cephem-4-carboxylate A solution of 1.56 g (5mM) of N-(3-chloropropylcarbonyl)-3-benzothienylglycine (prepared as described in Preparation 3) in 75 ml of acetonitrile and 25 ml of tetrahydrofuran containing 750 mg (5 mM) of hydroxybenzotriazole monohydrate was stirred at 25° C. while 1.24 g (6 mM) of N,N'-dicyclohexylcarbodiimide were added in one portion. The reaction mixture was stirred for two and one-half hours and then filtered. The filtrate was added in one portion to a solution of 1.65 g (5 mM) of p-nitrobenzyl 7-amino-3-methyl-3-cephem-4-carboxylate in 50 ml of acetonitrile containing 50 ml of tetrahydrofuran. The reaction mixture was stirred at 25° C. for seventeen hours, and then the precipitate that had formed was collected by filtration and identified as 834.8 mg (27% yield) of p-nitrobenzyl 7-[N-(3-chloropropylcarbonyl)-3-benzothienyl]glycylamido-3-methyl-3-cephem-4-carboxylate. NMR (DMSOd$_6$): $\delta$1.95 (m, 2H); $\delta$2.02 (br s, 3H); $\delta$2.30 (m, 2H); $\delta$3.2–3.75 (m, 4H); $\delta$5.12 (d, J=4.5, 1H); $\delta$5.42 (s, 2H); $\delta$5.78 (dd, J=4.5, 8.1, 1H); $\delta$6.09 (d, J=9, 1H); 7.4–8.4 (m, 9H); $\delta$8.68 (d, J=9, 1H); $\delta$9.38 (d, J=8.1, 1H).

EXAMPLE 2 p-Nitrobenzyl D,L-7-[N-p-nitrobenzyloxycarbonyl-(3-benzothienyl(-glycylamido]-3-methyl-3-cephem-4-carboxylate A solution of 3.86 g (10 mM) of D,L-N-p-nitrobenzyloxycarbonyl-(3-benzothienyl)glycine (prepared as described in Preparation 3) and 2.60 g (10.5 mM) of N-ethoxycarbonyl-2-ethoxy-1,2-dihydroquinoline in 25 ml of acetonitrile was stirred for five minutes at 25° C. and then was added to a solution of 3.84 g (11 mM) of p-nitrobenzyl 7-amino-3-methyl-3-cephem-4-carboxylate in 200 ml of tetrahydrofuran. The reaction mixture was stirred at 25° C. for sixteen hours, and the solvents were removed by evaporation to leave a white solid. The solid was dissolved in 1000 ml of dichloromethane and washed with water, twice with 150 ml portions of 5% aqueous sodium bicarbonate, twice with 5% hydrochloric acid, again with water and finally with brine. After drying the solution, the solvent was removed by evaporation to provide 5.49 g (76% yield) of p-nitrobenzyl D,L-7-[N-p-nitrobenzyloxycarbonyl-(3-benzothienyl)glycylamido]-3-methyl-3-cephem-4-carboxylate. NMR (DMSOd$_6$): $\delta$2.01 and 2.06 (two singlets, 3H, D and L isomers); $\delta$3.2–3.8 (m, 2H); $\delta$5.0 and 5.16 (two d, 1H); $\delta$5.21 (s, 2H); $\delta$5.3 (s, 2H); $\delta$5.6–5.9 (m, 2H); $\delta$7.2–8.5 (m, 13H); $\delta$9.2–9.4 (m, 1H).

EXAMPLE 3 p-Nitrobenzyl D,L-7-[N-tert.-butoxycarbonyl-(3-benzothienyl)-glycylamido]-3-methyl-3-cephem-4-carboxylate To a stirred solution of 19.25 g (55 mM) of p-nitrobenzyl 7-amino-3-methyl-3-cephem-4-carboxylate in 350 ml of tetrahydrofuran and 350 ml of acetonitrile was added in one portion a solution of 15.35 g (50 mM) of D,L-N-tert.-butoxycarbonyl-(3-benzothienyl)glycine in 350 ml of tetrahydrofuran containing 13 g of N-ethoxycarbonyl-2-ethoxy-1,2-dihydroquinoline. The reaction mixture was stirred at 25° C. for five and one-half hours, and then the solvent was removed by evaporation under reduced pressure to give an oil. The oil was dissolved in 500 ml of ethyl acetate and washed with 150 ml of water, twice with 150 ml portions of 5% sodium bicarbonate, twice with 150 ml portions of 5% hydrochloric acid, again with 150 ml of water and finally with 150 ml of brine. The solution was dried and the solvent was removed by evaporation to afford 30.45 g (95% yield) of p-nitrobenzyl D,L-7-[N-tert.-butoxycarbonyl-(3-benzothienyl)glycylamido]-3-methyl-3-cephem-4-carboxylate.

Analysis calc. for $C_{30}H_{30}N_4O_8S_2$: Theory: C, 56.41; H, 4.73; N, 8.77. Found: C, 56.45; H, 4,88; N, 8.61.

IR (KBr) 1774, 1522, 1348 cm$^{-1}$.

UV (CH$_3$OH) $\lambda_{225}$ $\epsilon$32,000 $\lambda_{265}$ $\epsilon$21,000.

NMR (DMSOd$_6$): $\delta$1.4 (s, 9H); $\delta$2.01 and 2.05; (two s, 3H); $\delta$3.28 (s, 1H); $\delta$3.48 (m, 2H); $\delta$5.10 (two d, 1H); $\delta$5.38 (s, 2H); $\delta$5.70 (m, 1H); $\delta$7.3–8.3 (m, 9H); $\delta$9.18 (m, 2H).

EXAMPLE 4 p-Nitrobenzyl 7-[N-tert.-butoxycarbonyl-(3-benzothienyl)-glycylamido]-3-chloro-3-3-cephem-4-carboxylate To a stirred solution of 406 mg (1.1 mM) of p-nitrobenzyl 7-amino-3-chloro-3-cephem-4-carboxylate in 10 ml of tetrahydrofuran and 10 ml of acetonitrile was added in one portion a solution of 307 mg (1 mM) of N-tert.-butoxycarbonyl-(3-benzothienyl)glycine in 10 ml of tetrahydrofuran containing 259 mg (1.05 mM) of N-ethoxycarbonyl-2-ethoxy-1,2-dihydroquinoline. The reaction mixture was stirred for twenty hours at 25° C., and then the solvent was removed by evaporation under reduced pressure to provide an oil. The oil was dissolved in 100 ml of ethyl acetate and washed with 50 ml of water, twice with 50 ml portions of 5% aqueous sodium bicarbonate, twice with 50 ml portions of 5% hydrochloric acid, and finally with another 50 ml portions of water. The organic layer was dried and concentrated to dryness by evaporation to afford 510 mg (79% yield) of p-nitrobenzyl 7-[N-tert.-butoxycarbonyl-(3-benzothienyl)glycylamido]-3-chloro-3-cephem-4-carboxylate. NMR (DMSOd$_6$): $\delta$1.40 (s, 9H); $\delta$3.81 (AB, 2H); $\delta$5.21 (d, J=4.5, 1H); $\delta$5.44 (s, 2H); $\delta$5.77 (d, J=9, 1H); $\delta$5.85 (dd, J=4.5, 9, 1H); $\delta$7.26–8.3 (m, 10H); $\delta$9.33 (d, J=9, 1H).

EXAMPLE 5 p-Nitrobenzyl 7-(3-benzothienyl)glycylamido-3-chloro-3-cephem-4-carboxylate

A solution of 620 mg (0.96 mM) of p-nitrobenzyl 7-[N-tert.-butoxycarbonyl-(3-benzothienyl)-glycylamido]-3-chloro-3-cephem-4-carboxylate in 25 ml of acetonitrile containing 250 mg (1.2 mM) of p-toluenesulfonic acid was stirred at 25° C. for ten minutes and then stored at 5° C. for sixteen hours. The reaction solvent was removed by evaporation under reduced pressure to provide p-nitrobenzyl 7-(3-benzothienyl)-glycylamido-3-chloro-3-cephem-4-carboxylate p-toluenesulfonic acid salt. NMR (DMSOd$_6$): $\delta$2.3 (s, 3H); $\delta$3.65, 3.92 (AB, J=18, 2H); $\delta$5.2 (d, J=5.4, 1H); $\delta$5.44 (s, 2H); $\delta$5.90 (dd, J=5.4, 8.1, 1H); $\delta$7.05–8.30 (m, 13H); $\delta$9.68 (d, J=8.1, 1H).

The product thus formed was dissolved in 25 ml of ethyl acetate and 25 ml of 10% aqueous sodium bicarbonate. The organic layer was removed, dried and the solvent was evaporated to give 230 mg of p-nitrobenzyl 7-(3-benzothienyl)glycylamido-3-chloro-3-cephem-4-carboxylate.

EXAMPLE 6

7-(3-Benzothienyl)glycylamido-3-chloro-3-cephem-4-carboxylic acid

A suspension of 230 mg of 5% palladium on carbon in 20 ml of ethanol was stirred at 25° C. for thirty minutes under hydrogen at 60 psi. To the stirred reaction mixture was added in one portion a solution of 230 mg of p-nitrobenzyl 7-(3-benzothienyl)glycyalmido-3-chloro-3-cephem-4-carboxylate (from Example 5) in 50 ml of methanol containing 1 ml of 1N hydrochloric acid and 2.5 ml of tetrahydrofuran. The reaction mixture was stirred at 25° C. for two hours under hydrogen at 60 psi. THe reaction mixture was then filtered and the filtrate was concentrated to about 2 ml. The solution was diluted with 10 ml of water and the pH was adjusted to 7.5 with 1N sodium hydroxide. After filtering the mixture, 1N hydrochloric acid was added to pH 4.25. The precipitated solid was collected by filtration and identified as 60 mg of 7-(3-benzothienyl)glycylamido-3-chloro-3-cephem-4-carboxylic acid. (78% D-isomer by high performance liquid chromatography). NMR (DMSOd$_6$): $\delta$3.38, 3.74 (AB, J=17.1, 2H); $\delta$5.02 (d, J=4.5, 1H); $\delta$5.31 (s, 1H); $\delta$5.65 (m, 1H); $\delta$7.2–8.1 (m, 5H); $\delta$8.6 (m, 1H).

EXAMPLE 7 p-Nitrobenzyl 7-(3-benzothienyl)glycylamido-3-methyl-3-cephem-4-carboxylate

A solution of 9.6 g (15 mM) of p-nitrobenzyl 7-[N-tert.-butoxycarbonyl-(3-benzothienyl)glycylamido]-3-methyl-3-cephem-4-carboxylate (prepared by the method of Example 3) in 210 ml of acetonitrile containing 3.42 g (18mM) of para-toluenesulfonic acid monohydrate was stored at 25° C. for three days. The precipitate that formed was collected by filtration and identified as p-nitrobenzyl 7-(3-benzothienyl)glycylamido-3-methyl-3-cephem-4-carboxylate para-toluenesulfonic acid salt monohydrate. The salt was dissolved in 60 ml of 10% aqueous sodium bicarbonate, and the solution was extracted several times with ethyl acetate. The extracts were combined, washed with water, dried and concentrated to dryness by evaporation under reduced pressure to give 7.9 g (76% yield) of p-nitrobenzyl 7-(3-benzothienyl)glycylamido-3-methyl-3-cephem-4-carboxylate. NMR (DMSOd$_6$): $\delta$1.99 and 2.04 (two singlets, 3H, D and L isomers); $\delta$3.2–3.6 (m, 2H); $\delta$4.9 (s, 2H); $\delta$5.1 (d, 1H); $\delta$5.36 (s, 2H); $\delta$5.7 (m, 1H); $\delta$7.3–8.25 (m, 10H).

EXAMPLE 8

7-(3-Benzothienyl)glycylamido-3-methyl-3-cephem-4-carboxylic acid

A solution of 5.2 g of p-nitrobenzyl 7-(3-benzothienyl)glycylamido-3-cephem-4-carboxylate (from Example 7) in 150 ml of methanol containing 10 ml of 1N hydrochloric acid and 5.2 g of 5% palladium on carbon was stirred at 25° C. for ninety minutes under 60 psi of hydrogen. The reaction mixture was filtered and the filtrate was concentrated to dryness to give a gum. The gum was dissolved in 40 ml of water and 40 ml of ethyl acetate. The mixture was neutralized to pH 7.0 by addition of 1N sodium hydroxide, and the organic layer was removed and discarded. The aqueous layer was acidified to pH 4.25 by addition of 1N hydrochloric acid. The aqueous acid solution was lyophilized to afford 1.62 g of D,L-7-(3-benzothienyl)glycylamido-3-methyl-3-cephem-4-carboxylic acid. Separation of the isomers was effected by high performance liquid chromatography (299.2 mg of d, 131.7 mg of L, 106.6 mg of D,L) NMR (DMSOd$_6$) of D-isomer $\delta$1.94 (s, 3H); $\delta$3.20 and 3.43 (AB, J=19.5, 2H); $\delta$4.96 (d, J=4.84, 1H); $\delta$5.07 (s, 1H); $\delta$5.62 (dd, J=4.4, 1H); $\delta$7.2–8.1 (m, 6H).

EXAMPLE 9

7-(3-Benzothienyl)glycylamido-3-methyl-3-cephem-4-carboxylic acid

A suspension of 1.4 g of 10% palladium on carbon in 50 ml of ethanol was stirred at 25° C. for thirty minutes under 60 psi of hydrogen. The suspension was then diluted by addition of a solution of 1.38 g of p-nitrobenzyl 7-(3-benzothienyl)glycylamido-3-methyl-3-cephem-4-carboxylate in 150 ml of methanol containing 20 ml of 1N hydrochloric acid. The reaction mixture was stirred at 25° C. under 60 psi of hydrogen for three hours. The catalyst was removed by filtration and the filtrate was concentrated to dryness to give a gum. The gum was suspended in 50 ml of water, and 1N sodium hydroxide was added to adjust the pH to 7.0. The insolubles were removed by filtration and the filtrate was acidified to pH 4.6 by addition of 1N hydrochloric acid. Lyophilization of the aqueous mixture afforded 64.3 mg (5.9%) of 7-(3-benzothienyl)glycylamido-3-methyl-3-cephem-4-carboxylic acid. NMR (DMSOd$_6$) was substantially identical to that reported in Example 8.

EXAMPLE 10 p-Nitrobenzyl 7-(3-benzothienyl)glycylamido-3-methyl-3-cephem-4-carboxylate

A solution of 1.54 g (2.5 mM) of p-nitrobenzyl-7-[N-(3-chloropropylcarbonyl)-3-benzothienyl]glycylamido-3-methyl-3-cephem-4-carboxylate (prepared as described in Example 1) in 250 ml of acetone, 125 ml of water and 200 ml of tetrahydrofuran was heated at reflux for five hours and then cooled to 25° C. The organic solvents were removed by evaporation and the aqueous mixture was acidified by addition of 2 ml of 1N hydrochloric acid and then filtered. The filtrate was diluted with 1N sodium hydroxide to pH 7.0, and the precipitate that formed was collected by filtration and dried to give 656 mg (51.6% yield) of p-nitrobenzyl 7-(3-benzothienyl)glycylamido-3-methyl-3-cephem-4-carboxylate. NMR (CDD1$_3$): $\delta$2.10 (s, 3H); $\delta$3.01–3.60 (AB, 2H); $\delta$4.91 (d, 1H), $\delta$4.96 (d, 1H); $\delta$5.25 (s, 2H); $\delta$5.75 (dd, 1H); $\delta$7.20–8.20 (m, 9H).

Hydrogenolysis of the compound thus formed provided 7-(3-benzothienyl)glycylamido-3-methyl-3-cephem-4-carboxylic acid.

EXAMPLE 11

D,L-Allyl 7-[N-allyloxycarbonyl-(3-benzothienyl)glycylamido]-3-methyl-3-cephem-4-carboxylate A solution of 5.82 g (20 mM) of D,L-N-allyloxycarbonyl-(3-benzothienyl)glycine (for example as prepared in Preparation 5) in 200 ml of tetrahydrofuran containing 5.18 g (21 mM) of N-ethoxycarbonyl-2-ethoxy-1,2-dihydroquinoline was added in one portion to a solution of 5.6 g (24 mM) of allyl 7-amino-3-methyl-3-cephem-4- carboxylate in 200 ml of acetonitrile. The reaction mixture was stirred at 25° C. for sixteen hours, and then concentrated to an oil by evaporation of the solvent. The oil was dissolved in 1 liter of ethyl acetate, washed once with 500 ml of water, twice with 250 ml portions of 5% aqueous sodium bicarbonate, twice with 5% hydrochloric acid, again with 250 ml of water, and finally with 250 ml of brine. The solution was dried and the solvent was removed by evaporation under reduced pressure to give 10.47 g (99% yield) of D,L-allyl 7-[N-alloyloxycarbonyl-(3-benzothienyl)glycylamido]-3-methyl-3-cephem-4-carboxylate.

Analysis calc. for $C_{25}H_{25}N_3O_6S_2$: Theory: C, 56.91; H, 4.70; N, 7.96. Found: C, 57.09; H, 4,94; N, 7.79.

NMR (DMSOd$_6$): δ2.00 and 2.05 (two singlets, 3H, D and L isomers); δ3.18–3.80 (m, 2H); δ4.45–6.10 (m, 13H); δ7.3–8.1 (m, 6H); δ9.1–9.35 (m, 1H).

EXAMPLE 12

D and L-7-(3-Benzothienyl)glycylamido-3-methyl-3-cephem-4-carboxylic acid

A solution of 72 mg (0.32 mM) of lead tetraacetate in 50 ml of acetone containing 4.19 mg (1.6 mM) of triphenylphosphine was stirred at 25° C. for thirty minutes, and then was cooled to 5° C. and diluted by addition of 30 ml of acetone containing 6.74 g (12.8 mM) of DL-allyl 7-N-allyloxycarbonyl-(3-benzothienyl)-glycylamido-3-methyl-3-cephem-4-carboxylate (from Example 11). The cold reaction mixture was stirred for ten minutes, and then 7.36 ml (28.2 mM) of tributyl tin hydride were added in one portion. The reaction mixture was stirred for one hour at 0°–5° C. and then was diluted by addition of 5 ml of 1N hydrochloric acid and stirred for an additional ten minutes. The reaction mixture was added to 25 ml of water and washed twice with 50 ml portions of n-hexane, and then the pH was adjusted to 4.5 wit 1N sodium hydroxide. Concentration of the solution by evaporation of the organic solvent effected precipitation of a product that was collected by filtration and lyophilized to provide 4.12 g (80% yield) of DL-7-(3-benzothienyl)glycylamido-3-methyl-3-cephem-4-carboxylic acid. A sample of the product thus formed (3.625 g) was purified further by high pressure liquid chromatography to give 522.5 mg of the L-isomer and 1.075 g of D-7-(3-benzothienyl)-glycylamido-3-methyl-3-cephem-4-carboxylic acid.

Analysis calc. for $C_{18}H_{17}N_3O_4S_2$: Theory: C, 53.58; H, 4.25; N, 10.41. Found: C, 53.94; H, 4.22; N, 10.62.

EXAMPLE 13

7-[α-Methoxyimino-α-(6-fluoro-3-benzothienyl)acetamido]-3-methyl-3-cephem-4-carboxylic acid A solution of 2.70 g (10.7 mM) of α-methoxy-α-(6-fluoro-3-benzothienyl)acetic acid (from Preparation 1) in 60 ml of benzene containing 2.8 ml of oxalyl chloride and 4 drops of N,N-dimethylformamide was stirred under nitrogen at 25° C. for two hours. The solvent was then removed by evaporation under reduced pressure to give α-methoxy-α-(6-fluoro-3-benzothienyl)acetyl chloride. The acid chloride was dissolved in 60 ml of acetone and added dropwise over five minutes to a stirred cold (5° C.) solution of 2.41 g (11.3 mM) of 7-amino-3-methyl-3-cephem-4-carboxylic acid in 60 ml of acetone and 120 ml of water containing 2.84 g (33.8 mM) of sodium bicarbonate. The reaction mixture was stirred for two hours at 5° C. and then warmed to 25° C. and stirred for an additional two hours. The reaction mixture was diluted with 1N hydrochloric acid to pH 7.5 and stored at 0° C. for twelve hours. Following removal of acetone from the reaction mixture by evaporation, the aqueous mixture was acidified to pH 2 with 1N hydrochloric acid, and the aqueous acid layer was extracted several times with dichloromethane. The organic extracts were combined, washed with brine, dried, and the solvent was removed by evaporation under reduced pressure to provide 5.02 g (100%) of 7-[α-methoxyimino-α-(6-fluoro-3-benzothienyl)acetamido]-3-methyl-3-cephem-4-carboxylic acid.

NMR (CDCl$_3$): δ2.24 (s, 3H); δ4.04 and 4.15 (two singlets, 3H); δ5.08 and 5.11 (two dd, 1H).

IR (CHCl$_3$) 1774 cm$^{-1}$ β-lactam.

EXAMPLES 14–16

By following the general procedure of Example 13, the following compounds were prepared:

7-[α-methoxyimino-α-(7-fluoro-3-benzothienyl)acetamido]-3-methyl-3-cephem-4-carboxylic acid.

IR (CHCl$_3$) 1782 cm$^{-1}$ β-lactum.

7-[α-methoxyimino-α-(4-fluoro-3-benzothienyl)acetamido]-3-methyl-3-cephem-4-carboxylic acid Analysis calc. for $C_{19}H_{16}N_3O_5S_2F$: Theory: C, 50.77; H, 3.59; N, 9.35; F, 4.23. Found: C, 50.93; H, 3.75; N, 9.07; F, 4.44.

NMR (CDCl$_3$): δ 2.22 (s, 3H); δ 4.04 (s, 3H); δ 5.09 (d, 1H); δ5.9 (dd, 1H); δ 6.98–7.63 (m, 6H).

7-[α-methoxyimino-α-(5-fluoro-3-benzothienyl)acetamido]-3-methyl-3-cephem-4-carboxylic acid IR (CHCl$_3$) 1778 cm$^{-1}$ β-lactam NMR (CDCl$_3$): δ 2.23 (s, 3H); δ 4.09 (s, 3H); δ 5.1 and 5.13 (two dd, 1H); δ 5.9 and 5.94 (two dd, 1H).

EXAMPLE 17

D-7-(6-Fluoro-3-benzothienyl)glycylamido-3-methyl-3-cephem-4-carboxylic acid

To a stirred cold (5° C.) solution of 5.01 g (11.1 mM) of 7-[α-methoxyimino-α-(6-fluoro-3-benzothienyl)acetamido]-3-methyl-3-cephem-4-carboxylic acid in 50 ml of methanol containing 25 ml of water and 50 ml of formic acid were added portionwise over twenty-five minutes 2.70 g (41.3 mM) of zinc dust. The reaction mixture was stirred for an additional two hours following complete addition, and then was filtered. The filtrate was concentrated to dryness by evaporation of the solvent under reduced pressure to provide a yellow gum. The gum was triturated with diethyl ether to afford, following drying in vacuum, 5.36 g of DL-7-(6-fluoro-3-benzothienyl)glycylamido-3-methyl-3-cephem-4-carboxylic acid. One gram of the product was purified by high pressure liquid chromatography over silica gel, eluting with an acetonitrileacetic acid gradient, to afford 149 mg of L, 60 mg of D,L and 318 mg of D-7-(6-fluoro-3-benzothienyl)glycylamido-3-methyl-3-cephem-4-carboxylic acid.

Analysis of the D-isomer calc. for $C_{18}H_{16}N_3O_4S_2F$: Theory: C, 51.30; H, 3.83; N, 9.97; F, 4.51. Found: C, 49.27; H, 3.97; N, 9.14; F, 4.48.

IR (CHCl$_3$): 1763 cm$^{-1}$ β-lactam.

EXAMPLES 18–21

By following the general procedure of Example 17, the following compounds were prepared:

D-7-(5-Fluoro-3-benzothienyl)glycylamido-3-methyl-3-cephem-4-carboxylic acid.

IR (CHCl₃): 1761 cm⁻¹ β-lactam.

NMR (DMSOd₆): δ 2.01 (s, 3H); δ 3.35 (dd, 2H); δ 2.8–4.2 (broad, 3H); δ 5.0 (s, 2H); δ 5.62 (d, 1H); δ 7.23 (m, 1H); δ 7.75–8.10 (m, 3H); δ 9.2 (broad, 1H).

D-7-(4-Fluoro-3-benzothienyl)glycylamido-3-methyl-3-cephem-4-carboxylic acid

NMR (DMSOd₆): δ 1.99 (s, 3H); δ 2.9–4.0 (broad m, 5H); δ 5.01 (s, 1H); δ 5.02 (d, 1H); δ 5.61 (d, 1H); δ 7.05–7.90 (m, 4H) δ 8.91 (broad, 1H).

D-7-(7-Fluoro-3-benzothienyl)glycylamido-3-methyl-3-cephem-4-carboxylic acid

NMR (DMSOd₆): δ 1.99 (s, 3H); δ 5.0 (m, 2H); δ 5.65 (d, 1H); δ 7.2–7.95 (m, 4H).

L-7-(7-Fluoro-3-benzothienyl)glycylamido-3-methyl-3-cephem-4-carboxylic acid

IR (CHCl₃): 1761 cm⁻¹ β-lactam

Analysis calc. for $C_{18}H_{16}N_3FO_4S_2$: Theory: C, 51.30; H, 3.83; N, 9.97; F, 4.51. Found: C, 49.79; H, 3.71; N, 9.64; F, 4.21.

EXAMPLE 22

7-[α-Methoxyimino-α-(6-methoxy-3-benzothienyl-)acetamido-3-methyl-3-cephem-4-carboxylic acid A solution of 610 mg (3.7 mM) of α-methoxyimino-α-(6-methoxy-3-benthienyl)acetic acid (from Preparation 8) in 50 ml of benzene containing 1.1 ml (12.6 mM) of oxalyl chloride and two drops of N,N-dimethylformamide was stirred at room temperature for one hour. The solvent was removed by evaporation under reduced pressure to provide α-methoxyimino-α-(6-methoxy-3-benzothienyl)acetyl chloride as an oil.

The product thus formed was dissolved in 40 ml of acetone and added dropwise over thirty minutes to a stirred cold (10° C.) solution of 830 mg (3.85 mM) of 7-amino-3-methyl-3-cephem-4-carboxylic acid in 40 ml of acetone and 75 ml of water containing 932 mg (11.1 mM) of sodium bicarbonate. The reaction mixture was warmed to 25° C. following the addition, and was stirred for an additional ninety minutes. The organic solvent was then removed by evaporation and the aqueous mixture was layered with ethyl acetate and made acidic to pH 2.5 with 1N hydrochloric acid. The organic layer was separated, washed with water, dried, and concentrated to dryness by evaporation to afford 856 mg of 7-[α-methoxyimino-α-(6-methoxy-3-benzothienyl)acetamido-3-methyl-3-cephem-4-carboxylic acid.

Analysis calc. for $C_{20}H_{19}N_3O_6S_2$: Theory: C, 52.06; H, 4.12; N, 9.11. Found: C, 51.79; H, 4.14; N, 8.77.

NMR (d₆DMSO): δ 2.02 (s, 3H); δ 3.34, 3.54 (AB, J=18.03, 2H); δ 3.83 (s, 3H); δ 3.98 (s, 3H); δ 5.13 (d, J=4.4, 1H); δ 5.74 (dd, J=4.4, 7.9, 1H); δ 7.05 (dd, J=2.4, 8.79, 1H); δ 7.59 (d, J=2.4, 1H); δ 7.65 (s, 1H); δ 8.41 (d, J=8.79, 1H); δ 9.73 (d, J=7.9, 1H).

EXAMPLE 23

D-7-(6-Methoxy-3-benzothienyl)glycylamido-3-methyl-3-cephem-4-carboxylic acid

To a cold (5° C.) stirred solution of 309 mg (0.67 mM) of 7-[α-methoxyimino-α-(6-methoxy-3-benzothienyl-)acetamido-3-methyl-3-cephem-4-carboxylic acid (from Example 22) in 0.5 ml of N,N-dimethylformamide and 10 ml of formic acid were added in one portion 170 mg (2.6 mM) of zinc metal dust. The reaction mixture was stirred for one hour and then was filtered through celite filter aid. The filter cake was washed twice with 10 ml portions of methanol, once with 10 ml of water, and again with 10 ml of methanol. The filtrate was then concentrated to dryness by evaporation of the solvent under reduced pressure, and the product was triturated with 25 ml of diethyl ether, and then suspended in 20 ml of water and lyophilized to provide 290 mg of DL-7-(6-methoxy-3-benzothienyl)glycylamido-3-methyl-3-cephem-4-carboxylic acid. This product was purified to separate the isomers by high pressure liquid chromatography to give 42.4 mg of D-7-(6-methoxy-3-benzothienyl)glycylamido-3-methyl-3-cephem-4-carboxylic acid. NMR (D₂O): δ 1.82 (s, 3H); δ 2.97, 3.40 (AB, J=17.9, 2H); δ 3.92 (s, 3H); δ 5.00 (d, J=4.3, 1H); δ 5.62 (s, 1H); δ 5.70 (d, J=4.3, 1H); δ 7.16–7.84 (m, 4H).

EXAMPLES 24–29

By following the general procedures set forth above, the following benzothienylglycyl cephalosporins are prepared:

7-(5-Chloro-3-benzothienyl)glycylamido-3-methyl-3-cephem-4-carboxylic acid 7-(6-Chloro-3-benzothienyl)glycylamido-3-methyl-3-cephem-4-carboxylic acid 7-(4,7-Dichloro-3-benzothienyl)glycylamido-3-methyl-3-cephem-4-carboxylic acid 7-(5-Methoxy-3-benzothienyl)glycylamido-3-methyl-3-cephem-4-carboxylic acid 7-(6-Hydroxy-3-benzothienyl)glycylamido-3-methyl-3-cephem-4-carboxylic acid 7-(6-Methylsulfonylamino-3-benzothienyl)-glycylamido-3-methyl-3-cephem-4-carboxylic acid

EXAMPLE 30

D-7-(3-Benzothienyl)glycylamido-3-methyl-3-cephem-4-carboxylic acid

D-(3-Benzothienyl)glycine (1.035 g (5 mM) from Preparation 6) was converted to D-N-tert.-butoxycarbonyl-3-benzothienylglycine by reaction with 1.2 ml (5.2 mM) of di-tert.-butyldicarbonate in 25 ml of tetrahydrofuran and 25 ml of water (yield 98%, 1.508). The procedure of Example 3 was followed to react 1.38 g (4.5 mM) of D-N-tert.-butoxycarbonyl-(3-benzothienyl)glycine with 1.73 g (4.9 mM) of p-nitrobenzyl 7-amino-3-methyl-3-cephem-4-carboxylate in the presence of 1.17 g (4.7 mM) of EEDQ to provide 2.673 g (93% yield) of p-nitrobenzyl D-7-[N-tert.-butoxycarbonyl-(3-benzothienyl)glycylamido]-3-methyl-3-cephem-4-carboxylate.

To a stirred solution of 2.55 g (4 mM) of the compound thus formed in 180 mg of acetonitrile were added in one portion 20 ml of acetonitrile containing 1.67 g (8.8 mM) of p-toluenesulfonic acid. The reaction mixture was stirred for three hours at 24° C. The precipitate that formed was collected by filtration (1.688 g), and the filtrate was concentrated to 25 ml and then chilled at 0° C. for forty-eight hours. Additional precipitate was collected by filtration (0.576 g), and the collected solids were combined and identified as 2.26 g (78% yield) of p-nitrobenzyl D-7-(3-benzothienyl)glycylamido-3-methyl-3-cephem-4-carboxylate p-toluenesulfonate monohydrate. The product was established as 100% pure D-isomer by NMR analysis. NMR (d₆DMSO): δ 1.97 (s, 3H); 2.28 (s, 3H); 3.30, 3.52 (AB, J=19.3, 2H); 3.32 (s, 2H); 5.05 (d, J=4.5, 1H); 5.36 (s, 2H); 5.46 (br s, 1H); 5.79 (dd, J=4.5, 8.1, 1H); 7.1–8.3 (m, 9H); 8.7 (br s, 3H); 9.58 (d, J=8.1, 1H).

A mixture of 2.20 g (3.03 mM) of the tosylate salt from above in 250 ml of dichloromethane and 200 ml of 5% aqueous sodium bicarbonate was stirred for five minutes. The organic layer was separated, dried and the solvent was removed by evaporation under reduced pressure to provide 1.607 g (98.5% yield) of p-nitrobenzyl D-7-(3-benzothienyl)glycylamido-3-methyl-3-cephem-4-carboxylate. The product was dissolved in 100 ml of methanol and 21 ml of ethanol and hydrogenated in the presence of 2.2 g of 5% palladium on carbon at room temperature for three hours under hydrogen at 60 psi. The reaction mixture was filtered to remove the catalyst, and the catalyst was washed with 10 ml of methanol containing 10 ml of water, and then three times with 10 ml portions of methanol. The filtrate was concentrated to a volume of about 20 ml, and then diluted with 10 ml of water and layered with 40 ml of ethyl acetate. The pH was adjusted to 7.0 by addition of 1N hydrochloric acid, and the aqueous layer was separated and made acidic to pH 4.6. The solution was stored at 5° C. for twelve hours, and then the white precipitate that had formed was collected by filtration and air dried to give 875 mg (73% yield) of D-(3-benzothienyl)glycylamido-3-methyl-3-cephem-4-carboxylic acid. High performance liquid chromatography established that the product was 100% pure D-isomer.

Analysis calc. for $C_{18}H_{17}N_3O_4S_2$: Theory: C, 53.58; H, 4.25; N, 10.41. Found: C, 53.20; H, 4.44; N, 9.88.

NMR ($D_2O/DCl$): $\delta$ 2.01 (s, 3H); $\delta$ 3.09, 3.33 (AB, J=18.1, 2H); $\delta$ 5.01 (d, J=4.6, 1H); $\delta$ 5.64 (d, J=4.4, 1H); $\delta$ 5.75 (s, 1H); $\delta$ 7.5–8.0 (m, 5H).

EXAMPLE 31

A suspension of 717 mg (1.0 mM) of p-nitrobenzyl D,L-7-[N-p-nitrobenzyloxycarbonyl-(3-benzothienyl)-glycylamido]-3-methyl-3-cephem-4-carboxylate (from Example 2) in 10 ml of ethanol and 100 ml of tetrahydrofuran containing 1.0 g of 5% palladium on carbon and 4.0 ml of 1N hydrochloric acid was stirred for three hours at 24° C. under hydrogen at 60 psi. The reaction mixture was filtered and the filtrate was diluted with water and then concentrated to about 20 ml, washed three times with 30 ml portions of ethyl acetate and then acidified to pH 4.3 by addition of 1N hydrochloric acid. Lyopholization of the acidic reaction mixture afforded D,L-7-(3-benzothienyl)glycylamido-3-methyl-3-cephem-4-carboxylic acid (15% yield). NMR ($D_2O/DCl$) established the product to be about 60% D and 40% L.

EXAMPLE 32

Separation of D and L isomers by chromatography

Two grams of p-nitrobenzyl D,L-7-[N-p-nitrobenzyloxycarbonyl-(3-benzothienyl)glycylamido]-3-methyl-3-cephem-4-carboxylate from Example 2 was dissolved in 500 ml of dichloromethane and slurried with 15 g of silica gel 60. The solvent was removed and the mixture was added to an 8 cm×15 cm column packed with 300 g of silica gel 60 in toluene. The column was eluted with a gradient of 2 liters of 5% ethyl acetate in toluene (v/v) to 2 liters of 20% ethyl acetate in toluene, and finally with 4 liters of 25% ethyl acetate in toluene. Twenty-five ml fractions were collected every two minutes. NMR and thin layer chromatographic analysis established that fractions 198–209 contained p-nitrobenzyl D-7-[N-p-nitrobenzyloxycarbonyl-(3-benzothienyl)-glycylamido]-3-methyl-3-cephem-4-carboxylate (347 mg, 35% yield); fractions 210–245 contained 1.163 g of the D,L-mixture; and fractions 246–276 contained 158 mg of the L-isomer.

The experiment was repeated employing a column packed with 350 g of silica gel 60 and eluting with a gradient of 2 liters of 10% (v/v) ethyl acetate in toluene to 2 liters of 20% of 20% ethyl acetate in toluene, and finally with 4 liters of 20% ethyl acetate in toluene. Fractions 201–226 were combined and concentrated to dryness to give 492 mg (49% yield) of p-nitrobenzyl D-7-[N-p-nitrobenzyloxycarbonyl-(3-benzothienyl)-glycylamido]-3-methyl-3-cephem-4-carboxylate.

EXAMPLE 33

D-7-(3-Benzothienyl)glycylamido-3-methyl-3-cephem-4-carboxylic acid

A solution of 772 mg (1.07 mM) of p-nitrobenzyl D-7-[N-p-nitrobenzyloxycarbonyl-(3-benzothienyl)-glycylamido]-3-methyl-3-cephem-4-carboxylate (from Example 32) in 90 ml of tetrahydrofuran and 12 ml of ethanol containing 4.5 ml of 1N hydrochloric acid and 1.2 g of 5% palladium on carbon was stirred for three hours at 25° C. under 60 psi of hydrogen. The reaction mixture was filtered and the filtrate was concentrated in volume, diluted with water and then lyopholized to give 273 mg of D-7-(3-benzothienyl)glycylamido-3-methyl-3-cephem-4-carboxylic acid. NMR was substantially identical to that reported in Example 8.

EXAMPLE 34 p-Nitrobenzyl D-7-[N-tert.-butoxycarbonyl-(3-benzothienyl)-glycylamido]-3-vinyl-3-cephem-4-carboxylate A solution of 451 mg (1.25 mM) of p-nitrobenzyl 7-amino-3-vinyl-3-cephem-4-carboxylate (prepared as described in U.S. Pat. No. 3,994,884) in 10 ml of tetrahydrofuran containing 415 mg (1.35 mM) of D-N-tert.-butoxycarbonyl-(3-benzothienyl)glycine and 358 mg (1.45 mM) of N-ethoxycarbonyl-2-ethoxy-1,2-dihydroquinoline was stirred at 25° C. for sixteen hours. The reaction mixture was concentrated to dryness to leave an oil, and the oil was dissolved in 50 ml of ethyl acetate and 50 ml of 10% aqueous sodium bicarbonate. The organic layer was separated, washed once with 10 ml of saturated sodium bicarbonate, once with water, twice with 10 ml portions of 1N hydrochloric acid, again with water, and finally with 10 ml of brine. The solution was dried and the solvent was removed by evaporation to give 700 mg (86% yield) of p-nitrobenzyl D-7-[N-tert.-butoxycarbonyl-(3-benzothienyl)glycylamido]-3-vinyl-3-cephem-4-carboxylate.

Analysis calc. for $C_{31}H_{30}N_4O_8S_2$: Theory: C, 57.22; H, 4.65; N, 8.61. Found: C, 57.52; H, 4.78; N, 8.55.

EXAMPLE 35

D-7-(3-Benzothienylglycylamido)-3-vinyl-3-cephem-4-carboxylic acid

To a stirred solution of 460 mg (0.7 mM) of p-nitrobenzyl D-7-[N-tert.-butoxycarbonyl-(3-benzothienyl)-glycylamido]-3-vinyl-3-cephem-4-carboxylate in 2.5 ml of water and 20 ml of methanol containing 5 ml of 98% formic acid were added in one portion 300 mg of zinc metal dust. The reaction mixture was sonicated for thirty minutes and filtered. The filtrate was diluted with 5 ml of water and extracted three times with 20 ml portions of ethyl acetate. The extracts were combined, washed with water and with brine, dried, and the solvent was removed by evaporation to provide 540 mg of a reddish solid. The solid was dissolved in 20 ml of dichloromethane and the solution was stored at 25° C. for twelve hours. The mixture was filtered and the filtrate was concentrated to dryness to give 320 mg of 7-D-[N-tert.-butoxycarbonyl-(3-benzothienyl)-glycylamido]-3-vinyl-3-cephem-4-carboxylic acid. NMR (DMSOd$_6$): δ 1.38 (s, 9H); δ 3.2–4.2 (m, 2H); δ 5.0–5.9 (m, 5H); δ 6.6–7.1 (m, 1H); δ 7.2–8.1 (m, 5H); δ 9.25 (d, 1H).

The product from above was dissolved in 10 ml of dichloromethane containing 1 ml of trifluoroacetic acid. The reaction mixture was stirred for two hours at 25° C. and then concentrated to dryness to provide 330 mg of an orange foam. The foam was dissolved in 10 ml of acetonitrile and the solution was diluted by dropwise addition of diisopropyl ether. The precipitate that formed was collected by filtration and air dried to give 190 mg of D-7-(3-benzothienylglycylamido)-3-vinyl-3-cephem-4-carboxylic acid trifluoroacetate.

UV (EtOH): λ$_{max}$ 225 ε 28,000;
IR (KBr): 1769 cm$^{-1}$ β-lactam
Analysis calc. for $C_{21}H_{18}N_3O_6S_2F_3$: Theory: C, 47.63; H, 3.43; N, 7.94; F, 10.76. Found: C, 47.86; H, 3.51; N, 8.18; F, 10.53.

EXAMPLE 36

D-7-(4-Chloro-3-benzothienyl)glycylamido-3-methyl-3-cephem-4-carboxylic acid

α-Methoxyimino-α-(4-chloro-3-benzothienyl)acetic acid was reacted with oxalyl chloride and N,N-dimethylformamide in benzene to give α-methoxyimino-α-(4-chloro-3-benzothienyl)acetyl chloride. A solution of 1.47 g (5.45 mM) of the acid chloride in 30 ml of acetone was added dropwise over ten minutes to a cold (5° C.) stirred solution of 1.22 g (5.7 mM) of 7-amino-3-methyl-3-cephem-4-carboxylic acid in 30 ml of water and 30 ml of acetone containing 1.37 g (16.35 mM) of sodium bicarbonate. The reaction mixture was stirred at 0°–5° C. for thirty minutes following the addition, and then was warmed to 20° C. and stirred for an additional two hours. The reaction mixture was concentrated to a volume of about 30 ml, diluted with 20 ml of water, and washed several times with ethyl acetate. The aqueous mixture was layered with 50 ml of fresh ethyl acetate and acidified to pH 2.5 by addition of 1N hydrochloric acid. The organic layer was separated, washed with fresh water and with brine, dried and the solvent was removed by evaporation to give 2.1 g (83% yield) of 7-[α-methoxyimino-α-(4-chloro-3-benzothienyl)acetamido]-3-methyl-3-cephem-4-carboxylic acid. NMR (DMSOd$_6$): δ 2.03 (s, 3H); δ 3.51 (broad s, 2H); δ 3.98 and 4.10 (two singlets, 3H); δ 5.11 (d, 1H); δ 5.68 (dd, 1H); δ 7.3–8.1 (m, 4H); δ 8.78 and 8.95 (two d, 1H).

To a cold (5° C.) stirred solution of 2.02 g (4.33 mM) of the methoxime from above in 21.5 ml of methanol, 21.5 ml of formic acid and 13.5 ml of water were added 1.05 g (16 mM) of zinc metal dust portionwise over thirty minutes. The reaction mixture was stirred thirty minutes at 5° C. and then was warmed to 25° C. and stirred for an additional five hours. The reaction mixture was stored at 0° C. for sixteen hours and then filtered. The solvents were removed from the filtrate to provide 1.79 g (95% yield) of a white powder identified as DL-7-(4-chloro-3-benzothienyl)glycylamido-3-methyl-3-cephem-4-carboxylic acid. High performance liquid chromatography over a $C_{18}$ reverse phase silica gel support, eluting with 2% acetic acid and a gradient of 5 to 25% (v/v) acetonitrile-water provided, following concentration and lyophilization of the appropriate fractions:

EXAMPLE 36A 169 mg of L-7-(4-chloro-3-benzothienyl)glycylamido-3-methyl-3-cephem-4-carboxylic acid; and

EXAMPLE 36B 190 mg of D-7-(4-chloro-3-benzothienyl)glycylamido-3-methyl-3-cephem-4-carboxylic acid. NMR (DMSOd$_6$): δ 2.01 (s, 3H); δ 3.1–3.7 (m, 2H); δ 4.7–5.9 (m, 7H); δ 7.3–8.1 (m, 4H).

EXAMPLE 37

Following the general procedure of Example 36, 2.8 g (10.39 mM) of α-methoxyimino-α-(6-chloro-3-benzothienyl)acetic acid were converted to the acid chloride and reacted with 2.33 g (10.91 mM) of 7-amino-3-methyl-3-cephem-4-carboxylic acid to provide 385 g (80% yield) of 7-[α-methoxyimino-α-(6-chloro-3-benzothienyl)acetamido]-3-methyl-3-cephem-4-carboxylic acid. NMR (CDCl$_3$): δ 2.02 and 2.21 (two s, 3H); δ 3.1–3.85 (m, 2H); δ 4.01 (s, 3H); δ 5.06 (d, 1H); δ 5.86 (dd, 1H); δ 7.2–7.8 (m, 4H); δ 8.3–8.7 (m, 2H).

Reduction of 3.83 g (8.2 mM) of the methoxime from above by reaction with 3.04 g of zinc metal dust in aqueous formic acid and methanol provided, following isolation, 4.6 g of a white powder. The product was chromatographed over a $C_{18}$ reverse phase silica gel column. High performance liquid chromatography provided:

EXAMPLE 37A 80 mg of L-7-(6-Chloro-3-benzothienyl)glycylamido-3-methyl-3-cephem-4-carboxylic acid; and

EXAMPLE 37B 49 mg of D-7-(6-chloro-3-benzothienyl)glycylamido-3-methyl-3-cephem-4-carboxylic acid. NMR (DMSOd$_8$): δ 1.95 (s, 3H); δ 3.05–3.65 (m, 2H); δ 4.5–6.0 (m, 6H); δ 7.3–8.2 (m, 4H).

EXAMPLE 38

7-(5-Chloro-3-benzothienyl)glycylamido-3-methyl-3-cephem-4-carboxylic acid

Reaction of chloroacetone with 4-chlorothiophenol gave (4-chlorophenyl)thiomethyl methyl ketone, which was cyclized by reaction with polyphosphoric acid to 5-chloro-3-methylbenzothiophene. Bromination of the latter compound by photochemical reaction with N-bromosuccinimide provided 5-chloro-3-bromomethylbenzothiophene, which was reacted with sodium cyanide to give 5-chloro-3-cyanomethylbenzothiophene. The latter compound was hydrolyzed and esterified to give methyl α-(5-chloro-3-benzothienyl)acetate. Reaction of the ester with sodium methoxide and n-butyl nitrite afforded methyl α-hydroxyimino-α-(5-chloro-3-benzothienyl)acetate. Reduction of the oxime by reaction with zinc and formic acid and subsequent reaction with di-tert.-butyl carbonate gave N-tert.-butoxycarbonyl-(5-chloro-3-benzothienyl)glycine. NMR (CDCl$_3$): δ 1.1–1.5 (broad s, 9H); δ 5.4–5.7 (broad s, 1H); δ 7.2–8.0 (m, 4H).

A solution of 766 mg (2.2 mM) of N-tert.-butoxycarbonyl-(5-chloro-3-benzothienyl)glycine and 844 mg (2.4 mM) of p-nitrobenzyl 7-amino-3-methyl-3-cephem-4-carboxylate in 380 ml of acetonitrile containing 544 mg (2.2 mM) of N-ethoxycarbonyl-2-ethoxy-1,2-dihydroquinoline was stirred at 0° C. for one hour and at 25° C. for four hours. The reaction mixture was concentrated to dryness by evaporation of the solvent, and the product was dissolved in 200 ml of ethyl acetate. The organic solution was washed with 1N hydrochloric acid, with saturated aqueous sodium bicarbonate, and with water. The solution was dried and the solvent was removed by evaporation under reduced pressure to give 1.28 g (87% yield) of p-nitrobenzyl D,L-7-[N-tert.-butoxycarbonyl-(5-chloro-3-benzothienyl)-glycylamido]-3-methyl-3-cephem-4-carboxylate. NMR (CDCl$_3$): δ 1.48 (s, 9H); δ 2.13 and 2.19 (two s, 3H); δ 3.1–3.5 (m, 2H); δ 4.9 and 5.01 (two sets doublets, 1H); δ 5.3 (broad s, 2H); δ 5.5–5.9 (m, 3H); δ 6.9–8.3 (m, 9H).

A suspension of 1.8 g of 5% palladium on carbon in 30 ml of methanol and 10 ml of ethanol was shaken for thirty minutes at 25° C. under 55 psi of hydrogen. A solution of 1.28 g of the compound from above in 100 ml of tetrahydrofuran was added to the reaction mixture, and the mixture was shaken at 25° C. for forty-five minutes under 57 psi of hydrogen. The reaction mixture was filtered and the solvent was removed from the filtrate. The product was dissolved in 50 ml of diethyl ether and 50 ml of water. The mixture was made alkaline to pH 7.7 and the organic layer was separated. The aqueous layer was washed with fresh diethyl ether, and then was made acidic to pH 2.0 by addition of 1N hydrochloric acid. The aqueous acid layer was extracted three times with 50 ml portions of ethyl acetate, and the extracts were combined, dried and concentrated to dryness to give 700 mg (70% yield) of D,L-7-[N-tert.-butoxycarbonyl-(5-chloro-3-benzothienyl)-glycylamido]-3-methyl-3-cephem-4-carboxylic acid. NMR (CDCl$_3$): δ 1.43 (s, 9H); δ 2.09 and 2.12 (two s, 3H); δ 3.1–3.5 (m, 2H); δ 4.8–5.3 (m, 1H); δ 5.4–6.1 (m, 3H); δ 7.0–8.4 (m, 7H).

A solution of 700 mg of the compound from above in 8 ml of trifluoroacetic acid was stirred at 25° C. for five minutes. The solution was added to 20 ml of water and the pH was adjusted to 6 by addition of 1N sodium hydroxide. The precipitate that formed was collected by filtration and air dried to give D,L-7-(5-chloro-3-benzothienyl)glycylamido-3-methyl-3-cephem-4-carboxylic acid. The isomers were separated by chromatography over a C$_{18}$ reverse phase silica gel column, eluting with a gradient of 1% acetic acid, 0 to 30% acetonitrile and 99 to 69% water. Appropriate fractions were combined, concentrated in volume by evaporation of solvents, and lyophilized to give:

EXAMPLE 38A

L-7-(5-chloro-3-benzothienyl)glycylamido-3-methyl-3-cephem-4-carboxylic acid; and

EXAMPLE 38B

D-7-(5-chloro-3-benzothienyl)glycylamido-3-methyl-3-cephem-4-carboxylic acid. NMR (DMSOd$_6$): δ 1.92 (s, 3H); δ 3.06–3.58 (q, 2H); δ 4.8–5.0 (broad d, 2H); δ 5.57 (d, 1H); δ 7.2–8.1 (m, 5H).

The benzothienylglycyl cephalosporins provided by this invention are valuable antibiotic substances, or intermediates therefor. The compounds are particularly effective against a wide variety of gram-positive bacilli, and are especially useful in the treatment of upper respiratory infections and similar diseases caused by *H. influenza, S. aureus, S. pyogenes,* and the like. The compounds are also effective in the treatment of diseases caused by anaerobic cocci such as *Peptostreptococcus anaerobius, Peptostrept. intermedius, Peptostrept. productus, Peptococcus osaccharolyticus, P. prevotii, P. avaerobius, Bacteroides fragilis, Propionibacterium acnes, Fusobacterium necrophorum,* and the like.

A typical and preferred compound provided by this invention is 7-(3-benzothienyl)glycylamido-3-methyl-3-cephem-4-carboxylic acid, the compound illustrated in Example 9. The antibacterial activity of this compound has been determined in standard in vitro agar dilution assays against a variety of gram positive and gram negative microorganism. The following Tables present typical minimum inhibitory concentrations (MIC's) in μg/ml for several compounds of the invention when evaluated against the indicated microorganisms. MIC's for several known compounds are also presented for comparison.

TABLE I

| Agar Dilution MIC (μg/ml) | | | | | | | | | | |
|---|---|---|---|---|---|---|---|---|---|---|
| | | Ampi- | Cepha- | Compound of | | | | | | |
| Organism | Strain | cillin | lexin | Ex. 9 | Ex. 17 | Ex. 18 | Ex. 19 | Ex. 20 | Ex. 21 | Ex. 22 |
| Staph. aureus | X1.1 | 0.25 | 4 | 1 | 1 | 1 | 4 | 0.5 | 32 | 1 |
| | V41 | 32 | 128 | 16 | 8 | 8 | 32 | 16 | 128 | 8 |
| | X400 | 128 | 128 | 64 | 64 | 64 | 128 | 128 | 128 | 64 |
| | S13E | 64 | 128 | 8 | 8 | 8 | 32 | 8 | 128 | 8 |
| Staph. epi | EPI1 | 8 | 32 | 8 | 4 | 8 | 32 | 4 | 128 | 8 |
| | 222 | 0.25 | 8 | 2 | 2 | 4 | 8 | 2 | 64 | 4 |
| Strep. A | C203 | 0.03 | 0.5 | 0.125 | 0.125 | 0.25 | 1 | 0.125 | 8 | 0.5 |
| Strep. PN | PARK | 0.03 | 2 | 0.5 | 0.5 | 1 | 4 | 0.5 | 16 | 0.5 |
| Strep. D | X66 | 4 | 128 | 128 | 128 | 128 | 128 | 128 | 128 | 64 |
| | 2041 | 2 | 128 | 64 | 64 | 128 | 128 | 128 | 128 | 64 |
| H. influ. | C.L. | 0.5 | 8 | 2 | 2 | 4 | 16 | 4 | 64 | 8 |
| | 76 | 16 | 8 | 0.5 | 0.5 | 1 | 4 | 0.5 | 8 | 2 |
| E. coli | N10 | 8 | 8 | 128 | 128 | 128 | 128 | 128 | 128 | 128 |
| | EC14 | 4 | 4 | 32 | 64 | 64 | 128 | 128 | 128 | 64 |
| | TEM | 128 | 8 | 32 | 64 | 64 | 128 | 128 | 128 | 128 |
| Klebsiella | X26 | 16 | 4 | 2 | 2 | 4 | 16 | 4 | 64 | 1 |
| | KAE | 128 | 128 | 128 | 128 | 128 | 128 | 128 | 128 | 128 |
| | X68 | 16 | 8 | 128 | 128 | 128 | 128 | 128 | 128 | 128 |
| | | Ampi- | Cepha- | Compound of | | | | | | |
| Organism | Strain | cillin | lexin | Ex. 35 | Ex. 36A | Ex. 36B | Ex. 37A | Ex. 37B | Ex. 38A | Ex. 38B |
| Staph. aureus | X1.1 | 0.25 | 4 | 2 | 64 | 16 | 16 | 1 | 8 | 1 |
| | V41 | 32 | 128 | 16 | 128 | 128 | 64 | 8 | 32 | 4 |
| | X400 | 128 | 128 | 32 | 128 | 128 | 128 | 16 | 64 | 8 |
| | S13E | 64 | 128 | 16 | 128 | 128 | 64 | 8 | 16 | 4 |

TABLE I-continued

| | | Agar Dilution MIC (µg/ml) | | | | | | | | |
|---|---|---|---|---|---|---|---|---|---|---|
| Staph. epi | EPI1 | 8 | 32 | 8 | 128 | 128 | 64 | 4 | 16 | 4 |
| | 222 | 0.25 | 8 | 2 | 64 | 8 | 32 | 2 | 16 | 2 |
| Strep. A | C203 | 0.03 | 0.5 | 0.125 | 16 | 8 | 4 | 0.5 | 1 | 0.25 |
| Strep. PN | PARK | 0.03 | 2 | 0.125 | 8 | 8 | 16 | 1 | 2 | 0.25 |
| Strep. D | X66 | 4 | 128 | 64 | 128 | 128 | 128 | 128 | 64 | 64 |
| | 2041 | 2 | 128 | 32 | 128 | 128 | 128 | 32 | 64 | 32 |
| H. influ. | C.L. | 0.5 | 8 | 8 | 128 | 128 | 128 | 8 | 32 | 8 |
| | 76 | 16 | 8 | 1 | 4 | 16 | 2 | 1 | 2 | 0.5 |
| E. coli | N10 | 8 | 8 | 128 | 128 | 128 | 128 | 128 | 64 | 64 |
| | EC14 | 4 | 4 | 128 | 128 | 128 | 128 | 128 | 64 | 64 |
| | TEM | 128 | 8 | 128 | 128 | 128 | 128 | 128 | 64 | 64 |
| Klebsiella | X26 | 16 | 4 | 8 | 128 | 128 | 64 | 4 | 16 | 2 |
| | KAE | 128 | 128 | 128 | 128 | 128 | 128 | 128 | 64 | 64 |
| | X68 | 16 | 8 | 128 | 128 | 128 | 128 | 128 | 64 | 64 |

TABLE II

Expanded Spectrum MIC (µg/ml)

| Organism | Strain | Ex. 9 | Ex. 17 | Ex. 18 | Ex. 19 | Ex. 20 | Ex. 22 |
|---|---|---|---|---|---|---|---|
| Staph. epi | EPI1 | 8 | 4 | 8 | 32 | 16 | 16 |
| | 270 | 4 | 2 | 4 | 16 | 8 | 8 |
| | 219 | 1 | 0.5 | 1 | 4 | 2 | 2 |
| | 269 | 2 | 2 | 4 | 16 | 4 | 4 |
| | 285 | 2 | 1 | 2 | 8 | 4 | 4 |
| | 286 | 1 | 0.25 | 1 | 1 | 1 | 1 |
| Staph. aureus | S224 | 1 | 1 | 1 | 4 | 2 | 2 |
| | S225 | 1 | 1 | 1 | 4 | 2 | 2 |
| | S226 | 2 | 1 | 2 | 4 | 2 | 2 |
| | S227 | 1 | 1 | 2 | 4 | 2 | 2 |
| | S228 | 1 | 0.5 | 1 | 4 | 2 | 2 |
| | S229 | 2 | 1 | 2 | 8 | 2 | 4 |
| | S230 | 1 | 1 | 1 | 4 | 2 | 2 |
| | S231 | 1 | 0.5 | 1 | 2 | 1 | 1 |
| | S234 | 2 | 1 | 2 | 4 | 2 | 2 |
| | S237 | 1 | 1 | 2 | 4 | 2 | 2 |
| | S238 | 2 | 1 | 2 | 8 | 4 | 4 |
| | S239 | 2 | 1 | 2 | 8 | 2 | 2 |
| H. influenzae | C.L. | 2 | 2 | 2 | 16 | 16 | 4 |
| | 76 | 1 | 1 | 1 | 4 | 1 | 1 |
| | HESS | 1 | 1 | 2 | 16 | 8 | 4 |
| | STEL | 64 | 64 | 64 | 64 | 64 | 64 |
| | 312 | 1 | 0.5 | 1 | 8 | 4 | 1 |
| | R465 | 64 | 64 | 64 | 64 | 64 | 2 |

TABLE II-continued

Expanded Spectrum MIC (µg/ml)

| Organism | Strain | Ex. 9 | Ex. 17 | Ex. 18 | Ex. 19 | Ex. 20 | Ex. 22 |
|---|---|---|---|---|---|---|---|
| | 1930 | 1 | 0.5 | 1 | 16 | 4 | 1 |
| | 4842 | 1 | 0.5 | 1 | 8 | 2 | 1 |
| | 1683 | 0.5 | 0.25 | 0.25 | 2 | 1 | 0.5 |
| | M366 | 64 | 64 | 64 | 64 | 64 | 64 |
| | M370 | 1 | 0.5 | 1 | 4 | 2 | 1 |
| | M371 | 1 | 0.5 | 1 | 4 | 2 | 2 |
| | 105 | 1 | 0.5 | 1 | 4 | 2 | 2 |
| | 158 | 1 | 0.5 | 1 | 4 | 2 | 1 |
| | 164 | 1 | 0.5 | 1 | 4 | 2 | 1 |
| | 171 | 1 | 1 | 1 | 4 | 2 | 2 |
| | 169 | 1 | 1 | 1 | 4 | 4 | 2 |

TABLE III

Susceptibility of Anaerobic Bacteroides Isolates by the Agar-Dilution Method MIC (µg/ml) readings 24 hrs. after incubation

| Anaerobic bacteria | Strain | moxalactam | Ex. 9 | Ex. 17 | Ex. 18 | Ex. 19 | Ex. 20 |
|---|---|---|---|---|---|---|---|
| Bacteroides fragilis | 1877 | 2 | 8 | 8 | 16 | 8 | 16 |
| | 103 | 4 | 32 | 16 | 64 | 32 | 64 |
| | 104 | 0.5 | 4 | 2 | 16 | 16 | 8 |
| | 106 | 1 | 4 | 4 | 16 | 8 | 16 |
| | 107 | 1 | 8 | 8 | 16 | 8 | 32 |
| | 108 | 0.5 | 4 | 4 | 16 | 16 | 8 |
| | 110 | 0.5 | 8 | 4 | 16 | 8 | 32 |
| | 111 | 8 | 64 | 32 | 128 | 64 | 128 |
| | 9 | 0.5 | 4 | 4 | 8 | 8 | 16 |
| Bacteroides corrodens | 1874 | 8 | 32 | 16 | 64 | 32 | 64 |
| Bacteroides thetaiotaomicron | 1438 | 2 | 4 | 8 | 16 | 16 | 16 |
| | 1900A | 64 | 16 | 32 | 32 | 32 | 32 |

The excellent activity of the compounds against anaerobic bacteria and against *Haemophilus influenzae* has been further demonstrated in expanded tests employing more strains of microorganism. The compound of Example 9 was compared to known antibiotics and proved to be much more potent than those with which it was compared. Table IV presents typical MIC values obtained against a wide variety of strains of *Bacteroides fragilis* and *H. influenzae*.

TABLE IV

Expanded anaerobic and *H. influenzae* Spectrum MIC (µg/ml)

| Microorganism | Strain | cephalexin | cefaclor | Compound A[1] | Compound B[2] |
|---|---|---|---|---|---|
| Bacteroides fragilis | 10817 | 16 | 64 | 0.5 | 4 |
| | 180-821 | 16 | 64 | 0.5 | 2 |
| | 10695 | 64 | 32 | 0.5 | 16 |
| | 107268 | 16 | 16 | 2 | 16 |
| | 107266 | 32 | 16 | 0.5 | 4 |
| | 10750 | 64 | >64 | 8 | 64 |
| | 10774 | >64 | >64 | 1 | 64 |
| | 10837 | 16 | >64 | 0.5 | 16 |

TABLE IV-continued

| | | Expanded anaerobic and *H. influenzae* Spectrum MIC (μg/ml) | | | |
|---|---|---|---|---|---|
| Microorganism | Strain | cephalexin | cefaclor | Compound A[1] | Compound B[2] |
| | 10732 | 32 | 16 | 0.5 | 4 |
| | 10683 | >64 | 16 | 0.5 | 16 |
| | 10668 | >64 | 64 | 0.5 | 64 |
| | 108133 | 32 | 32 | 0.5 | 16 |
| | mean | 40 | 39 | 1.2 | 27 |
| | Standard Deviation | 22 | 23 | 2.1 | 26 |
| | Geometric mean | 34 | 32 | 0.7 | 15 |
| Haemophilus | 101 | 8 | 2 | 1 | 2 |
| influenzae | 102 | 16 | 16 | 16 | 16 |
| | 103 | 16 | 2 | 0.5 | 2 |
| | 104 | 16 | 1 | 1 | 2 |
| | 105 | 4 | 1 | 0.5 | 2 |
| | 106 | 8 | 2 | 1 | 1 |
| | 107 | 8 | 2 | 1 | 4 |
| | 108 | 8 | 1 | 2 | 1 |
| | 109 | 16 | 2 | 1 | 1 |
| | 110 | 8 | 1 | 0.5 | 4 |
| | 111 | 16 | 1 | 0.5 | 1 |
| | 112 | 16 | 2 | 2 | 8 |
| | 113 | 8 | 2 | 0.5 | 2 |
| | 114 | 8 | 1 | 2 | 2 |
| | mean | 22 | 3 | 2.1 | 3 |
| | Standard Deviation | 42 | 4 | 3.9 | 4 |
| | Geometric Mean | 12 | 2 | 1.1 | 2 |

[1]7-(3-benzothienyl)glycylamido-3-methyl-3-cephem-4-carboxylic acid
[2]7-(2-benzothienyl)glycylamido-3-methyl-3-cephem-4-carboxylic acid The data in the above Tables clearly demonstrate the potent antibacterial activity possessed by the compounds of this invention.

In addition to possessing potent antibacterial activity against a wide variety of microorganisms, particularly gram positive organisms and anaerobes, the compounds of this invention also have demonstrated very favorable pharmacokinetics in animals. For example, when 7-(3-benzothienylglycylamido)-3-methyl-3-cephem-4-carboxylic acid was administered to rats at an intravenous dose of 20 mg/kg, the plasma concentration after one hour was 25.0 μg/ml, and after four hours, 10.5 μg/ml.

The compounds of the invention also have good stability to β-lactamases. Table IV shows the results of comparative studies of several cephalosporins (lower numbers mean greater stability to the indicated β-lactamase).

TABLE V

| | Stability to β-lactamase | | | | |
|---|---|---|---|---|---|
| | Organism | | | | |
| | 265A | PS185 | TEM | 1082E | 1313G |
| cefaclor | 138 | 71 | 23 | 65 | 4605 |
| cephalexin | 72 | 37 | 1 | 6 | 254 |
| 7-(3-benzothienyl-glycylamido)3-methyl-3-cephem-4-carboxylic acid | 14 | 25 | 3 | 25 | 210 |

The favorable pharmacokinetics of the compounds provided by this invention, coupled with their excellent antibacterial activity and oral absorption, make them particularly attractive agents for the treatment of a number of diseases of bacterial origin. The compounds are especially well suited for the treatment of outpatients, and especially for subjects suffering from mild upper respiratory infections caused by gram positive microorganisms.

The treatment of animals suffering from bacterial diseases, or suspected of developing a bacterial infection, is thus another embodiment of this invention. The antibacterial method of treatment provided by this invention will be practiced by administering an antibacterially effective amount of a benzothienylglycyl cephalosporin antibiotic as defined herein to an animal in need of treatment. The method can be practiced therapeutically or prophylactically. The amount of active antibiotic to be administered according to the method will vary depending upon the particular compound selected for use, the severity of the disease being treated or guarded against, the individual undergoing treatment, and related factors commonly encountered with such treatments. Normally, however, the compounds will be administered at a dose of about 0.5 to about 50 mg/kg of animal body weight, and more preferably at a rate of about 1 to about 10 mg/kg. Such amounts will be administered once each day, or more often as needed to treat the particular disease or subject undergoing treatment according to the present method. A typical daily dose for an average adult human will be about 200 to about 500 mg per day.

The antibiotic compounds provided by this invention are active by both the oral and parenteral routes of administration, and accordingly can be formulated for any such desired route of administration. Such formulations constitute yet another embodiment of this invention. The formulations of this invention will comprise from about 0.1 to about 95 percent by weight of an active benzothienylglycyl cephalosporin antibiotic of the invention, admixed with a pharmaceutically acceptable carrier, diluent or excipient therefor. Typical formulations will contain from about 10 to about 60 percent by weight of active ingredient, and more preferably about 20 to about 50 percent.

For convenient oral administration, the compounds can be admixed with any of a number of diluents, excipients and carriers commonly employed in oral formulations, and molded into tablets, pills, troches, or encapsulated into gelatin capsules. Typical carriers, diluents and excipients commonly employed include potato starch, corn starch, sucrose, dextrose, microcrystalline cellulose, dicalcium phosphate, alginic acid, acacia; lubricants such as magnesium stearate; binders such as gum tragacanth or gelatin; and flavoring agents such as peppermint oil, cherry or strawberry flavoring, oil of wintergreen, and the like. The compounds can also be formulated as syrups or elixirs employing common diluents such as a fatty oil, methyl or propyl parabens, suitable dyes and flavoring agents. The compounds can also be formulated in the form of a buccal seal, logenze or other suitable device for sustained controlled delivery of the active ingredient over a prolonged period.

The antibiotics of the invention can also be formulated for parenteral administration, for example via the intravenous, intramuscular or subcutaneous routes, as well as the transdermal route. Such compositions normally will contain from about 0.1 to about 20.0 percent by weight of active ingredient. Typical excipients, diluents and carriers for parenteral formulations include isotonic saline, dilute aqueous dextrose, the polyhydric aliphatic alcohols or mixtures thereof, for instance glycerin, propylene glycol, polyethylene glycol, and the like. Parenteral solutions may also contain preservatives such as phenethylalcohol, methyl and propyl parabens, thimerosal and the like. If needed, about 0.05 to about 0.20 percent by weight of an antioxidant such as sodium metabisulfite or sodium bisulfite can also be employed. For intravenous use, preferred formulations will employ an initial concentration down to about 0.05 to about 0.25 mg/ml of active ingredient, and for intramuscular injection, a preferred concentration of active ingredient is about 0.25 to about 0.50 mg/ml.

Examples of typical pharmaceutical formulations contemplated by this invention include the following.

EXAMPLE 39

Formulation of Oral Suspension

| Ingredient | Amount |
|---|---|
| Sodium D-7-(3-benzothienylglycylamido)-3-chloro-3-cephem-4-carboxylate | 500 mg |
| Sorbitol solution (70% N.F.) | 40 ml |
| Sodium benzoate | 150 mg |
| Saccharin | 10 mg |
| Cherry flavor | 50 mg |
| Distilled water q s ad | 100 ml |

The sorbitol solution is added to 40 ml of distilled water and the benzothienylglycyl cephalosporin is suspended thereon. The saccharin, sodium benzoate, and flavoring are added and dissolved. The volume is adjusted to 100 ml with distilled water. Each ml of syrup contains 5 mg of the benzothienylglycyl cephalosporin antibiotic. This oral formulation is ideally suited for pediatric use.

EXAMPLE 40

Preparation of 250 mg capsule

| Ingredient | Amount |
|---|---|
| 7-(6-Chloro-3-benzothienylglycylamido)-3-methyl-3-cephem-4-carboxylic acid | 250 mg |
| Lactose | 150 mg |
| Corn starch | 100 mg |
|  | 500 mg |

The ingredients are blended to uniformity and encapsulated into gelatin capsules. Such capsules are orally administered at the rate of about one each day for the treatment of upper respiratory bacterial infections, including pharyngitis and tonsillitis.

EXAMPLE 41

Preparation of Parenteral Solution

In a solution of 700 ml of propylene glycol and 200 ml of distilled water for injection is dissolved 20.0 grams of D-7-(3-benzothienylglycylamido)-3-methoxymethyl-3-cephem-4-carboxylic acid, hydrochloride. The pH of the solution is adjusted to 5.5 with hydrochloric acid, and the volume is made up to 1000 ml with distilled water. The formulation is sterilized, filled into 5.0 ml ampoules each containing 2.0 ml (representing 40 mg of active ingredient) and sealed under nitrogen.

I claim:

1. A compound of the formula

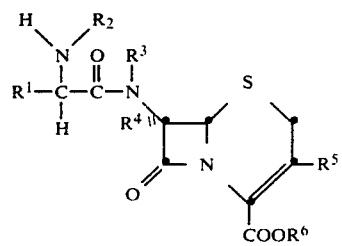

wherein:

$R^1$ is

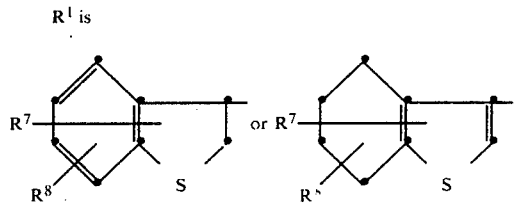

in which $R^7$ and $R^8$ independently are hydrogen, halo, hydroxy, $C_1$–$C_4$ alkyl, $C_1$–$C_4$ alkoxy, nitro, amino, $C_1$–$C_4$ alkanoylamino, $C_1$–$C_4$ alkylsulfonylamino, and when $R^7$ and $R^8$ are on adjacent carbon atoms, they can be taken together to form methylenedioxy;

$R^2$ is hydrogen, an amino protecting group, and $R^3$ is hydrogen, or $R^2$ and $R^3$ taken together are

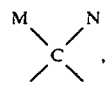

where M and N independently are $C_1$–$C_4$ alkyl;

$R^4$ is hydrogen, methoxy or methylthio;

$R^5$ is hydrogen, methoxy, methyl, halo, methoxymethyl, or vinyl;

$R^6$ is hydrogen, a salt forming cation group, or a carboxy protecting group; and the pharmaceutically acceptable acid addition salts thereof.

2. The compound of claim 1 wherein $R^2$ and $R^3$ are taken together to form

3. The compound of claim 1 wherein $R^1$ is

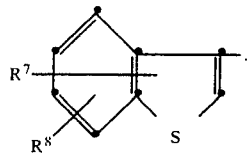

4. The compound of claim 3 wherein $R^7$ is hydrogen or halo.
5. The compound of claim 4 wherein $R^7$ is hydrogen.
6. The compound of claim 5 wherein $R^4$ is hydrogen.
7. The compound of claim 6 wherein $R^5$ is methyl or chloro.
8. The compound of claim 7 wherein $R^6$ is hydrogen or a salt forming cation.
9. The compound of claim 8, said compound being D-7-(3-benzothienyl)glycylamido-3-methyl-3-cephem-4-carboxylic acid.
10. The compound of claim 8 wherein $R^8$ is halo.
11. The compound of claim 10 wherein $R^8$ is chloro.
12. The compound of claim 10 wherein $R^8$ is fluoro.
13. The compound of claim 8 wherein $R^8$ is hydroxy.
14. The compound of claim 8 wherein $R^8$ is $C_1-C_4$ alkoxy.
15. The compound of claim 8 wherein $R^8$ is amino.
16. The compound of claim 6 wherein $R^5$ is hydrogen.
17. The compound of claim 6 wherein $R^5$ is methoxymethyl.
18. The compound of claim 6 wherein $R^5$ is vinyl.
19. The compound of claim 1 wherein $R^1$ is

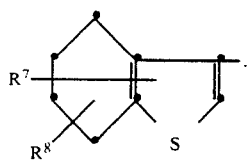

20. The compound of claim 19 wherein $R^7$ is hydrogen.
21. The compound of claim 20 wherein $R^4$ is hydrogen.
22. The compound of claim 21 wherein $R^5$ is methyl or chloro.

23. The compound of claim 22 wherein $R^6$ is hydrogen or a salt forming cation.
24. A method of treating bacterial infections in animals comprising administering an effective amount of an antibacterial compound of claim 1.
25. The method of claim 24 employing a compound wherein $R^2$, $R^3$ and $R^4$ all are hydrogen.
26. The method of claim 25 employing a compound wherein $R^6$ is hydrogen or a salt forming cation.
27. The method of claim 26 employing a compound wherein $R^5$ is methyl or chloro.
28. The method of claim 27 employing a compound wherein $R^1$ is

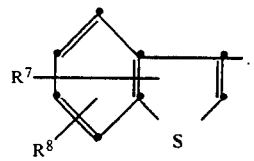

29. The method of claim 28 employing a compound wherein $R^7$ is hydrogen.
30. The method of claim 29 employing D-7-(3-benzothienyl)glycylamido-3-methyl-3-cephem-4-carboxylic acid.
31. The method of claim 29 employing a compound wherein $R^8$ is fluoro.
32. The method of claim 29 employing a compound wherein $R^8$ is chloro.
33. A pharmaceutical formulation useful for treating bacterial infections comprising an antibacterially effective amount of a compound of claim 1 admixed with a pharmaceutical carrier, diluent or excipient therefor.
34. The formulation of claim 33 employing a compound wherein $R^2$, $R^3$ and $R^4$ all are hydrogen.
35. The formulation of claim 34 employing a compound wherein $R^6$ is hydrogen or a salt forming cation.
36. The formulation of claim 35 employing a compound wherein $R^5$ is methyl or chloro.
37. The formulation of claim 36 employing a compound wherein $R^1$ is

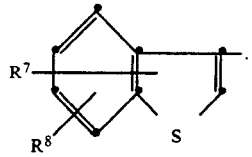

38. The formulation of claim 37 employing a compound wherein $R^7$ is hydrogen.
39. The formulation of claim 38 employing a compound wherein $R^8$ is hydrogen.
40. The formulation of claim 38 employing a compound wherein $R^8$ is halo.

* * * * *

UNITED STATES PATENT AND TRADEMARK OFFICE
CERTIFICATE OF CORRECTION

PATENT NO. : 4,492,693
DATED : January 8, 1985
INVENTOR(S) : Larry C. Blaszczak et al.

Page 1 of 2

It is certified that error appears in the above—identified patent and that said Letters Patent is hereby corrected as shown below:

Column 1, lines 30-35, that portion of the formula which reads

" 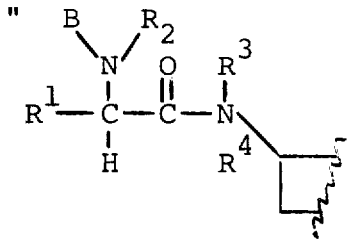 " should read -- 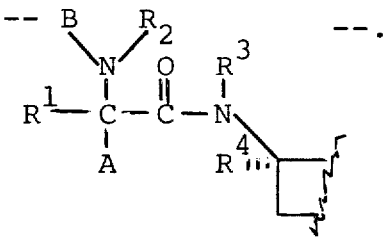 --.

Column 1, lines 45-47, that portion of the formula which reads

"  " should read --  --.

Column 1, lines 45-50, that portion of the formula which reads

" 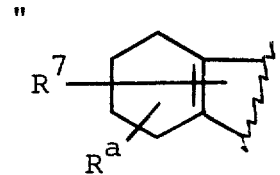 " should read -- 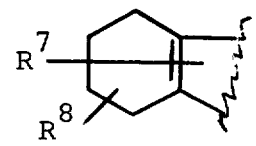 --.

Column 22, line 23, "3-chloro-3-3-cephem" should read
--3-chloro-3-cephem--.

UNITED STATES PATENT AND TRADEMARK OFFICE
CERTIFICATE OF CORRECTION

PATENT NO. : 4,492,693
DATED : January 8, 1985
INVENTOR(S) : Larry C. Blaszczak et al.

Page 2 of 2

It is certified that error appears in the above—identified patent and that said Letters Patent is hereby corrected as shown below:

Column 24, line 6, "(299.2 mg of d," should read --(299.2 mg of D,--.

Column 25, line 24, "4.19 mg" should read --419 mg--.

Column 40, lines 37-40, that portion of the formula which reads

" 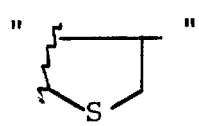 "    should read    -- 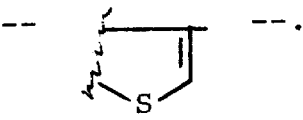 --.

*Signed and Sealed this*

*Sixth* Day of *August 1985*

[SEAL]

Attest:

DONALD J. QUIGG

Attesting Officer

Acting Commissioner of Patents and Trademarks